United States Patent [19]
Kontos

[11] Patent Number: 6,077,276
[45] Date of Patent: Jun. 20, 2000

[54] DEVICE AND METHOD FOR SUTURING BLOOD VESSELS AND THE LIKE

[75] Inventor: Stavros Kontos, Woodcliff Lake, N.J.

[73] Assignee: X-Site L.L.C., Totowa, N.J.

[21] Appl. No.: 09/251,640

[22] Filed: Feb. 17, 1999

Related U.S. Application Data

[62] Division of application No. 08/960,486, Oct. 29, 1997.

[51] Int. Cl.⁷ ................................................ A61B 17/04
[52] U.S. Cl. ........................ 606/144; 606/145; 606/228
[58] Field of Search ................................... 606/139, 144, 606/145, 147, 148, 228, 232, 233; 112/169

[56] References Cited

U.S. PATENT DOCUMENTS

| | | |
|---|---|---|
| 3,807,407 | 4/1974 | Schweizer . |
| 4,107,953 | 8/1978 | Casillo ..................................... 66/1 R |
| 4,493,323 | 1/1985 | Albright et al. . |
| 4,757,827 | 7/1988 | Buchbinder et al. . |
| 4,799,495 | 1/1989 | Hawkins et al. . |
| 4,841,888 | 6/1989 | Mills et al. . |
| 4,890,615 | 1/1990 | Caspari et al. . |
| 5,037,433 | 8/1991 | Wilk et al. . |
| 5,080,663 | 1/1992 | Mills et al. . |
| 5,108,421 | 4/1992 | Fowler . |
| 5,304,184 | 4/1994 | Hathaway et al. . |
| 5,312,360 | 5/1994 | Behl . |
| 5,312,423 | 5/1994 | Rosenbluth et al. ..................... 606/148 |
| 5,320,632 | 6/1994 | Heidmueller . |
| 5,324,306 | 6/1994 | Makower . |
| 5,336,229 | 8/1994 | Noda . |
| 5,336,231 | 8/1994 | Adair . |
| 5,364,408 | 11/1994 | Gordon . |
| 5,368,601 | 11/1994 | Sauer et al. . |
| 5,374,275 | 12/1994 | Bradley et al. . |
| 5,383,896 | 1/1995 | Gershony et al. . |
| 5,387,221 | 2/1995 | Bisgaard . |
| 5,391,182 | 2/1995 | Chin . |
| 5,391,183 | 2/1995 | Janzen et al. . |
| 5,403,329 | 4/1995 | Hinchcliffe . |
| 5,431,666 | 7/1995 | Sauer et al. ............................. 606/139 |
| 5,437,631 | 8/1995 | Janzen . |
| 5,447,502 | 9/1995 | Haaga . |
| 5,458,609 | 10/1995 | Condon et al. . |
| 5,474,543 | 12/1995 | McKay . |
| 5,476,469 | 12/1995 | Hathaway et al. . |
| 5,527,322 | 6/1996 | Klein . |
| 5,578,044 | 11/1996 | Gordon et al. . |
| 5,676,689 | 10/1997 | Kensey . |
| 5,700,273 | 12/1997 | Buelna et al. . |

(List continued on next page.)

FOREIGN PATENT DOCUMENTS

| | | |
|---|---|---|
| 0 637 431 | 2/1995 | European Pat. Off. . |
| 95/13021 | 5/1995 | WIPO . |

Primary Examiner—Michael Buiz
Assistant Examiner—Lien Ngo
Attorney, Agent, or Firm—Kenyon & Kenyon

[57] ABSTRACT

A method and device for sealing an opening in an anatomical structure within a living body involves the positioning of the tissue adjacent to the opening within a gap between proximal and distal parts of a tube formed by a curved central part. A needle coupled to a suture is pushed from a needle retention channel formed within the proximal part through the tissue received in the gap and into a needle receiving channel formed within the distal part. The device may be moved to a second position where a new region of tissue is located in the gap between the proximal and distal parts of the tube. The needle may be pushed or drawn out of the receiving channel in the distal part, through the tissue and into the receiving channel in the proximal part to thereby loop the suture through the anatomical structure. The procedure may be repeated to form multiple suture loops in the structure and then the ends of the suture may be knotted.

Needle pushing mechanisms may be adapted to move through the needle retention channels, and thus may be used to push a needle through the device. The device may include a trigger mechanism which is adapted to move the needle pushing mechanisms and thus the needle may be placed through the anatomical structure through operation of the trigger mechanism.

13 Claims, 28 Drawing Sheets

U.S. PATENT DOCUMENTS

| | | |
|---|---|---|
| 5,713,910 | 2/1998 | Gordon et al. . |
| 5,720,757 | 2/1998 | Hathaway et al. . |
| 5,728,133 | 3/1998 | Kontos . |
| 5,755,727 | 5/1998 | Kontos .................................. 606/144 |
| 5,766,183 | 6/1998 | Sauer ..................................... 606/139 |
| 5,779,719 | 7/1998 | Klein et al. . |
| 5,792,151 | 8/1998 | Heck et al. ............................ 606/144 |
| 5,792,152 | 8/1998 | Klein et al. . |
| 5,792,153 | 8/1998 | Swain et al. ........................... 606/144 |
| 5,810,849 | 9/1998 | Kontos . |
| 5,810,850 | 9/1998 | Hathaway et al. . |
| 5,814,065 | 9/1998 | Diaz ....................................... 606/213 |
| 5,830,125 | 11/1998 | Scribner et al. . |
| 5,843,098 | 12/1998 | Allen et al. . |
| 5,846,253 | 12/1998 | Buelna et al. . |
| 5,855,585 | 1/1999 | Kontos . |
| 5,876,411 | 3/1999 | Kontos . |
| 5,902,311 | 5/1999 | Andreas et al. . |
| 5,910,155 | 6/1999 | Ratcliff et al. . |
| 5,921,994 | 7/1999 | Andreas et al. . |
| 5,928,266 | 7/1999 | Kontos . |

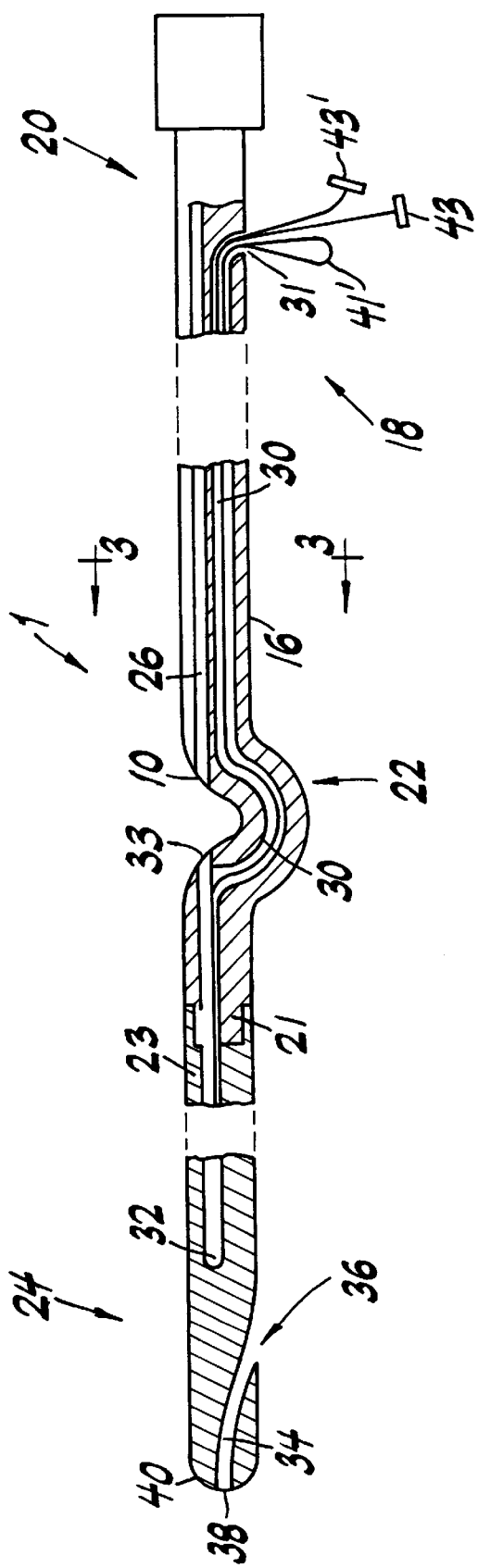
FIG. 1
FIG. 3A
FIG. 3B

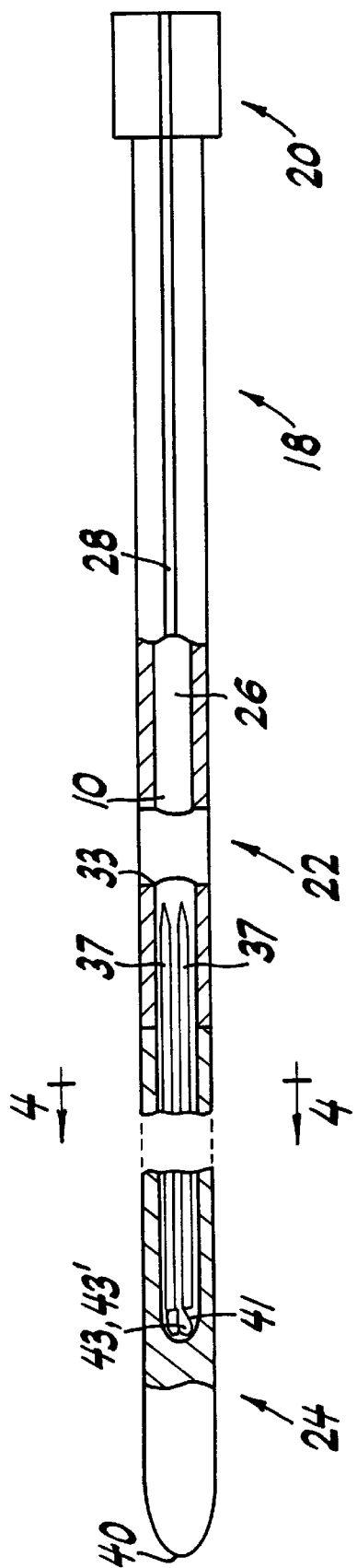
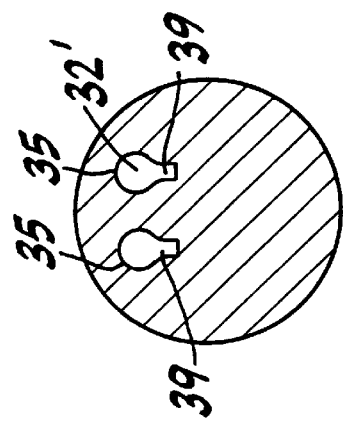
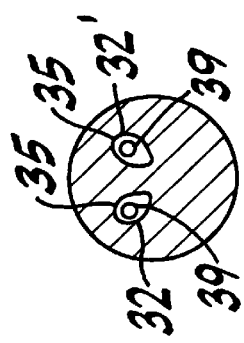
FIG. 2
FIG. 4A
FIG. 4B

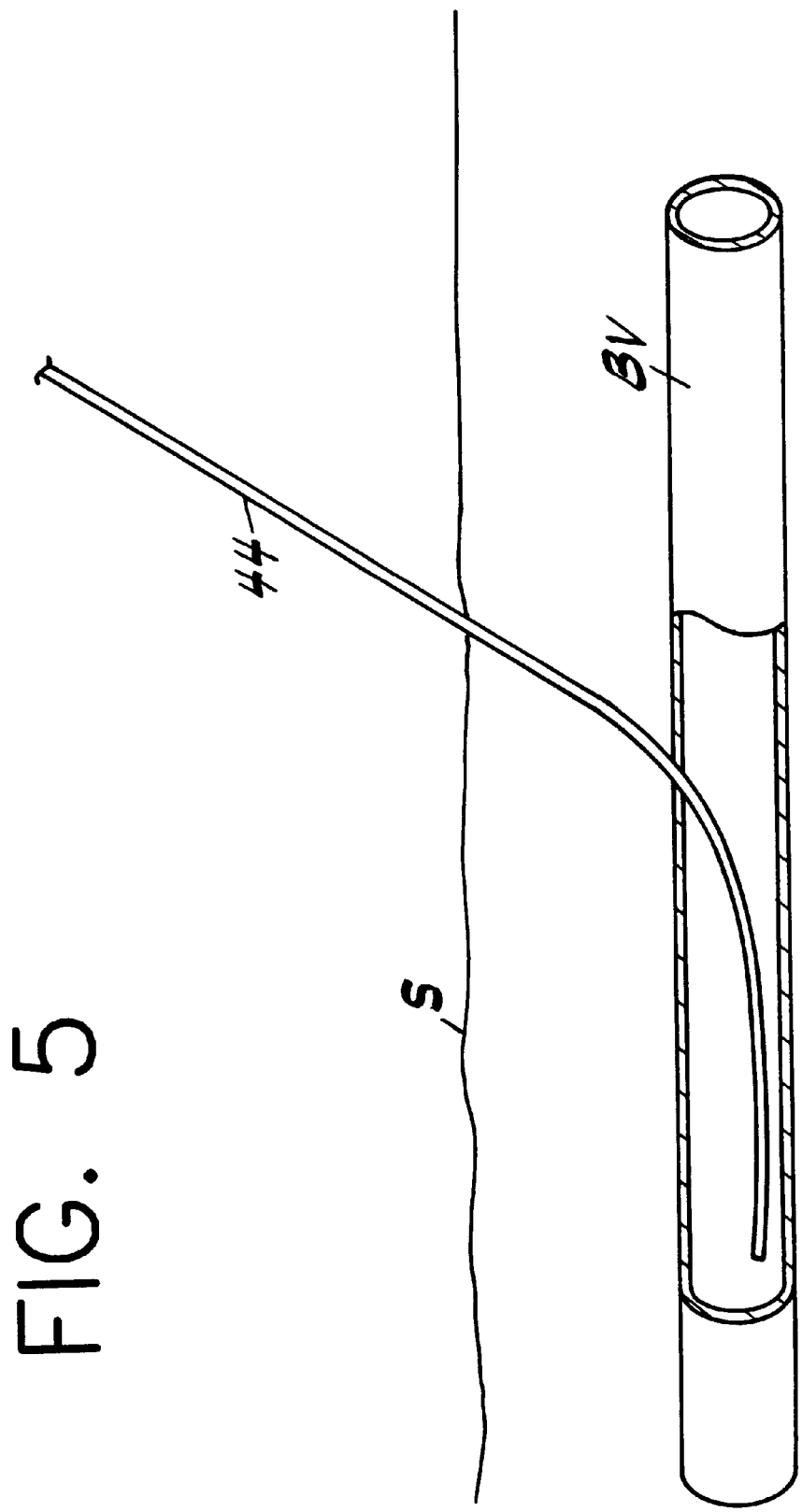

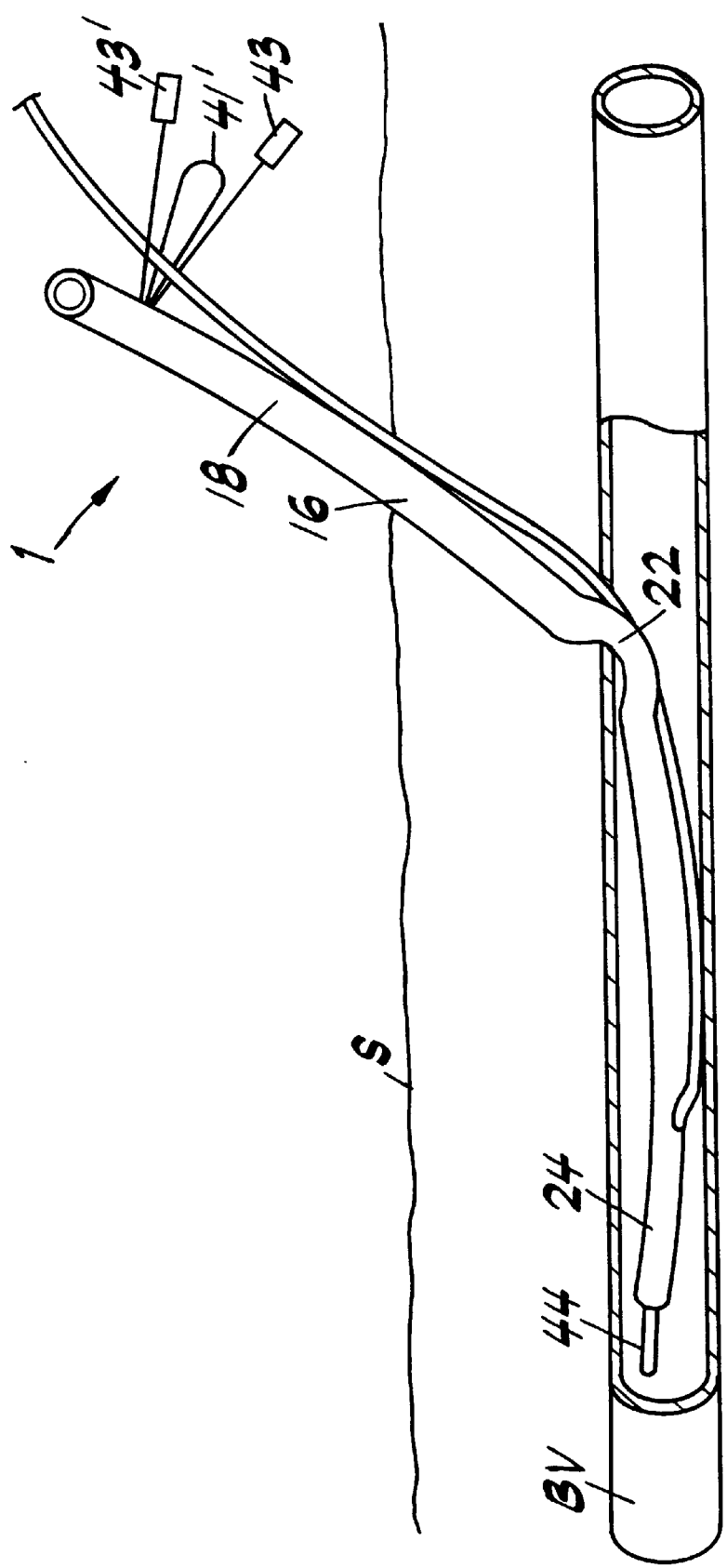

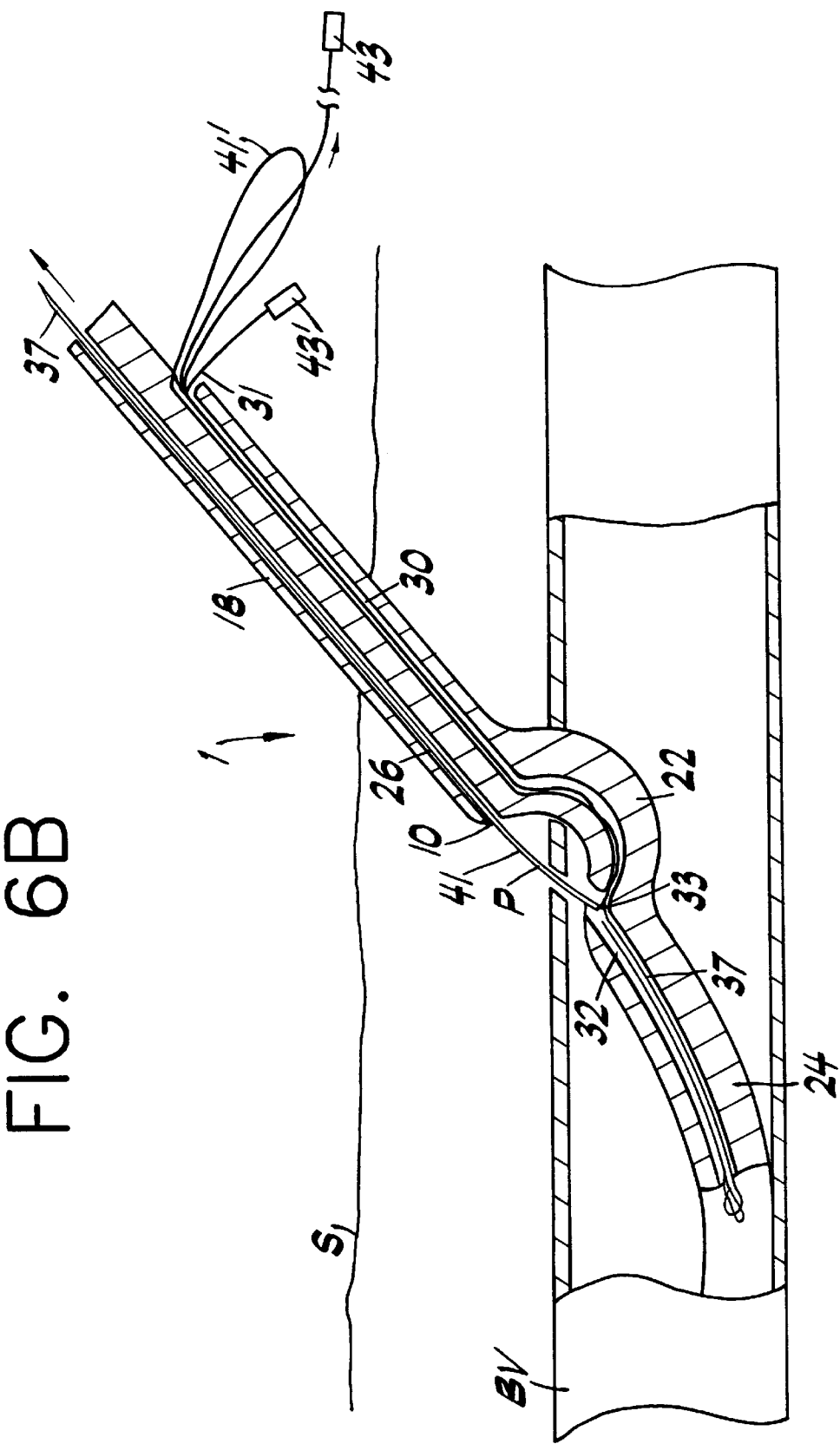

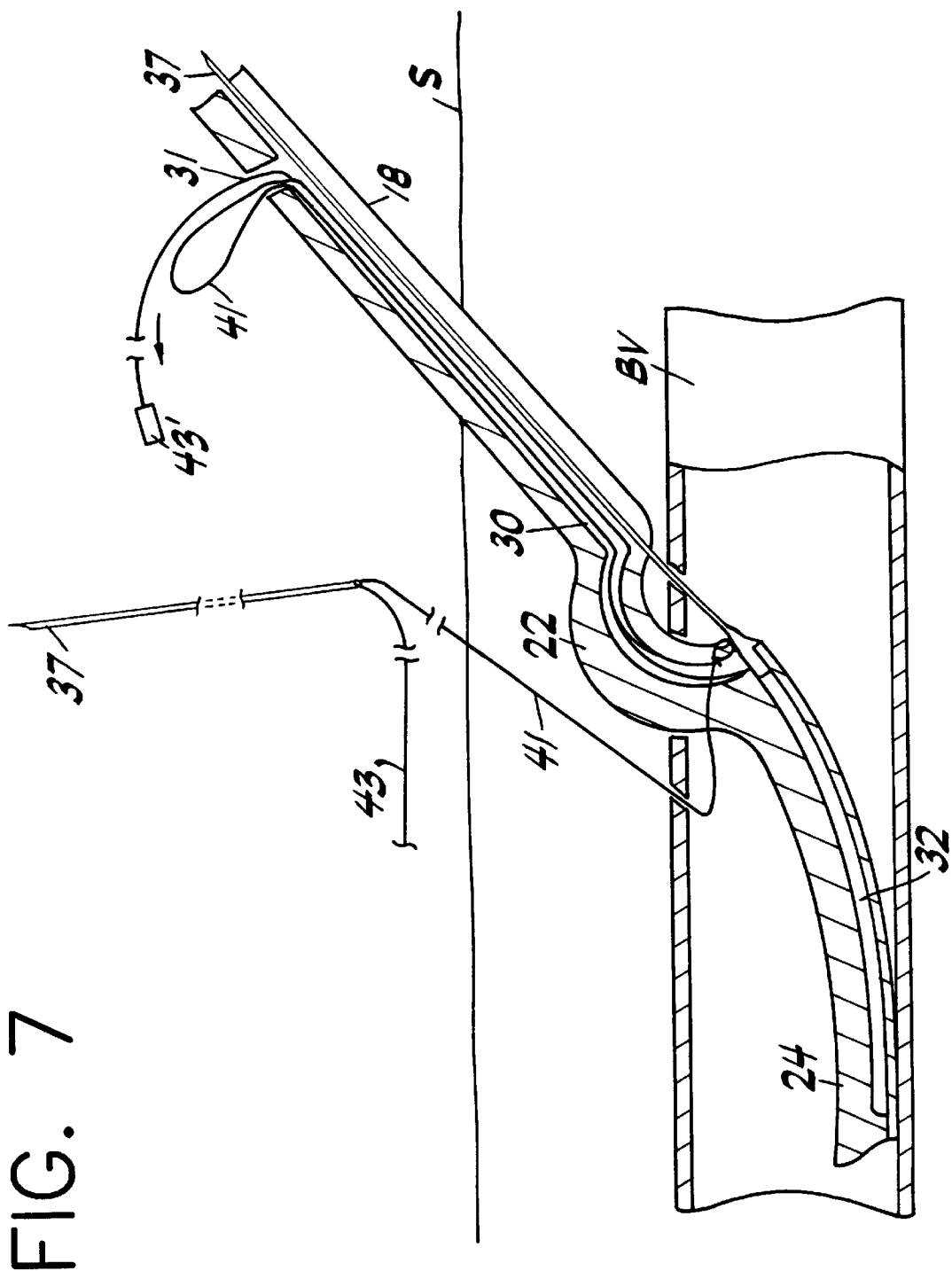

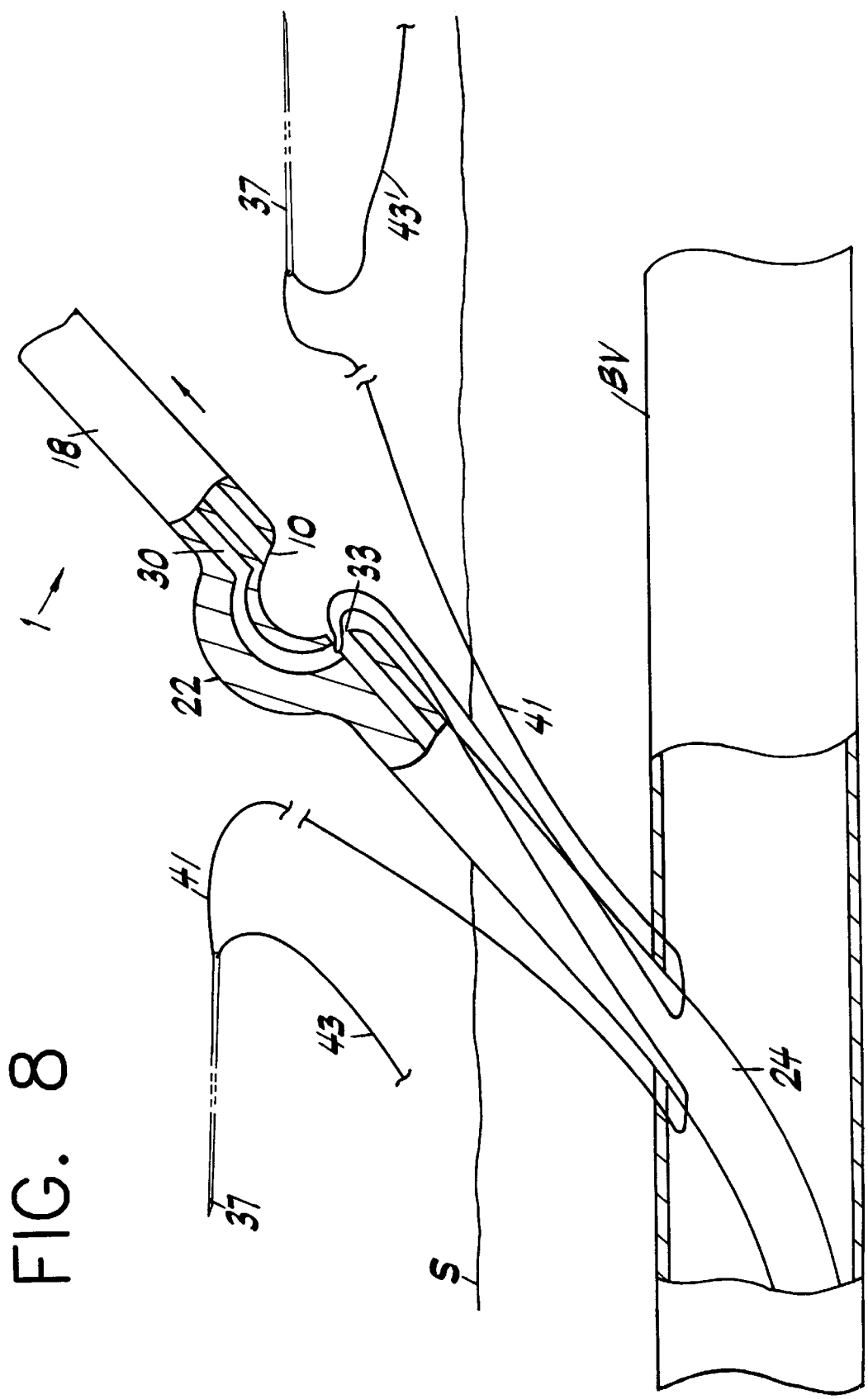

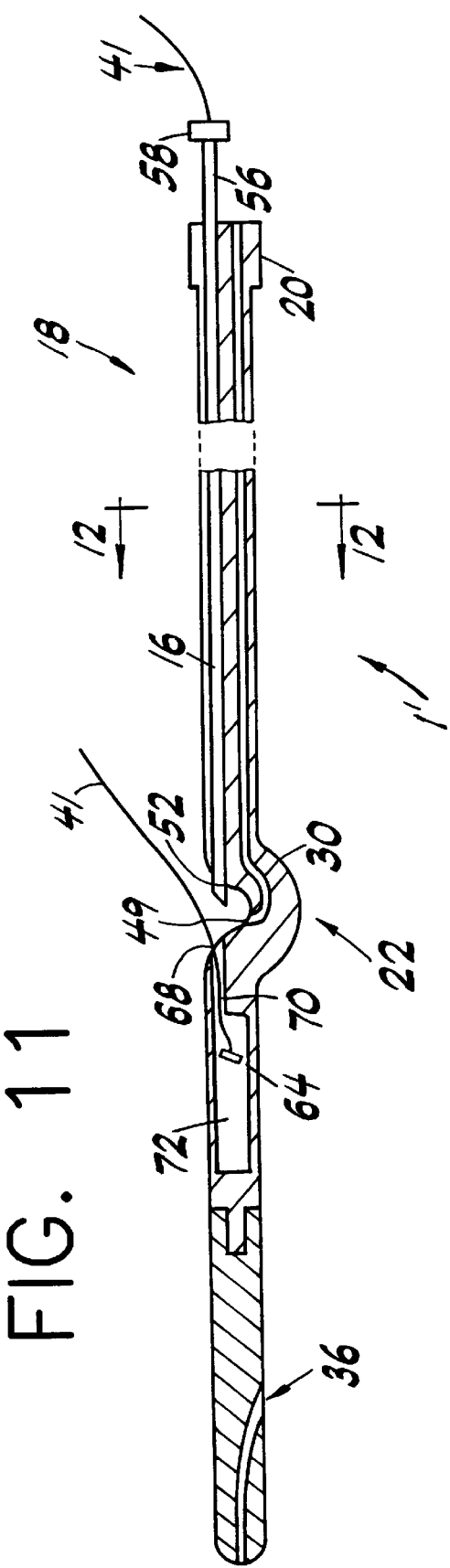

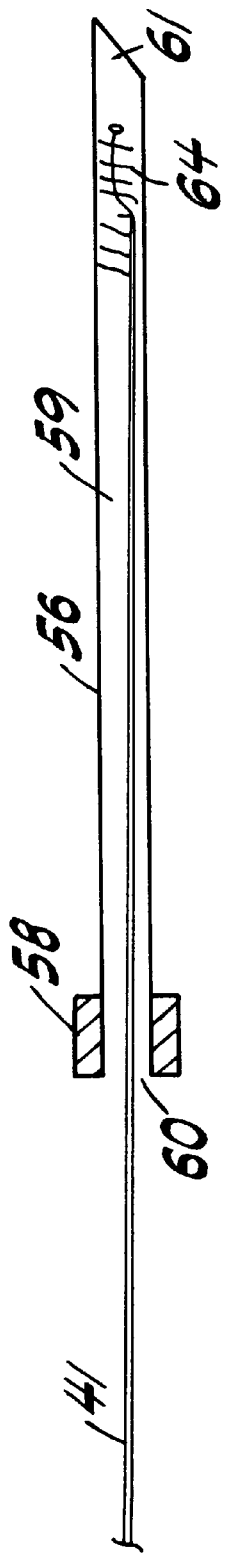
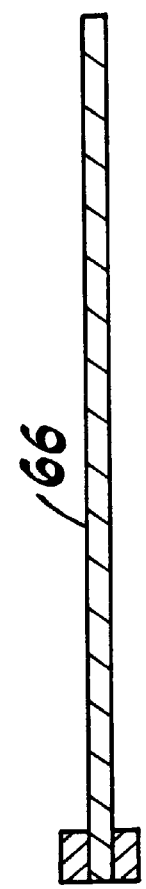
FIG. 13
FIG. 14

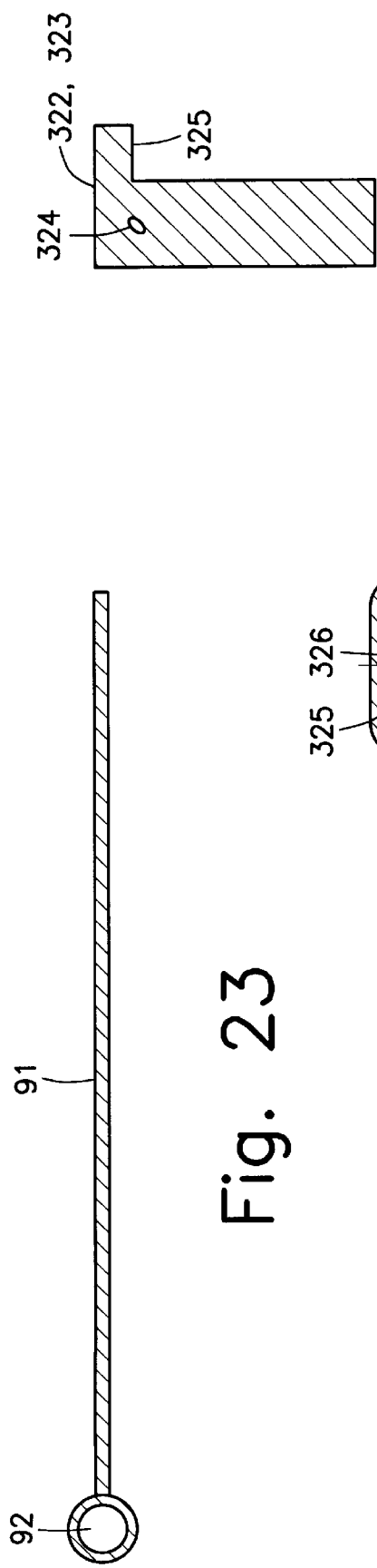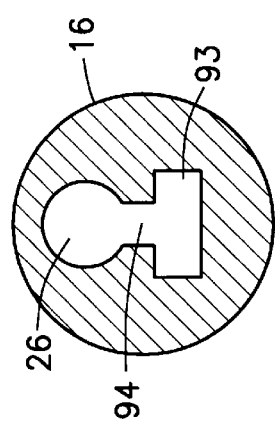

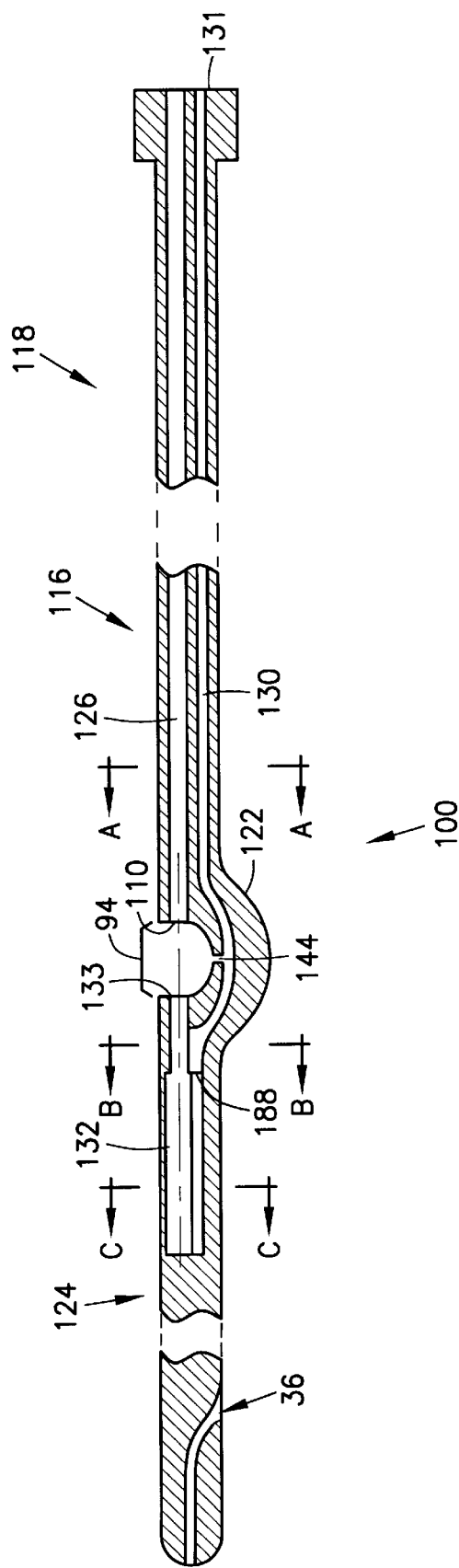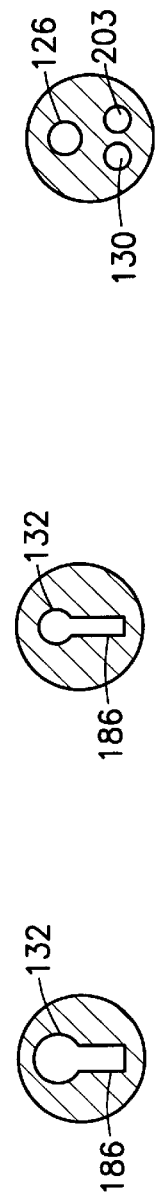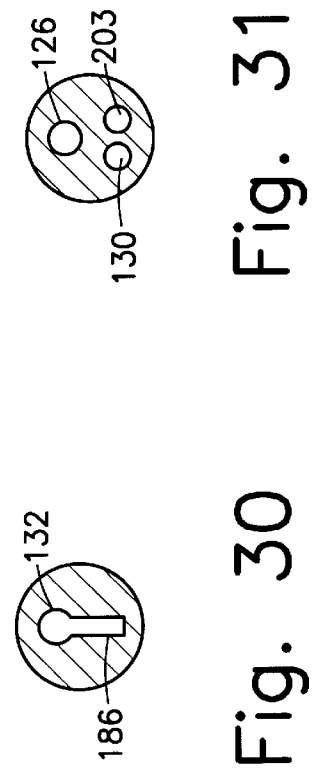
Fig. 28
Fig. 29
Fig. 30
Fig. 31

DEVICE AND METHOD FOR SUTURING BLOOD VESSELS AND THE LIKE

CROSS-REFERENCE TO RELATED APPLICATION

This application is a divisional application of prior application Ser. No. 08/960,486, filed Oct. 29, 1997.

FIELD OF THE INVENTION

The present invention relates generally to surgical instruments, and more specifically to devices for the suturing of punctures in blood vessels, internal organs and internal tissues accessed via a tissue tract.

BACKGROUND OF THE INVENTION

Many surgical procedures require the insertion of catheters and/or surgical devices into blood vessels and other internal structures. For example, in the treatment of vascular disease, it is often necessary to insert an instrument, i.e., a catheter, into the blood vessel to perform the treatment procedure. Such treatment procedures often involve piercing a wall of the blood vessel, inserting an introducer sheath into the blood vessel via the opening, and maneuvering the procedural catheter through the introducer sheath to a target location within the blood vessel. Of course in order to complete such a procedure, the sides of the opening in the wall of the blood vessel must be sealed to prevent bleeding while facilitating healing of the wound. At present, this sealing is commonly accomplished by application of direct pressure over the puncture site by a physician or other trained medical professional. Due to the dangers of thrombosis, the substantial reduction of blood flow through the blood vessel due to the application of pressure is undesirable and potentially dangerous to the patient. In addition, the procedure is extremely time consuming; often requiring that pressure be applied for forty-five minutes or more to achieve acceptable sealing.

Other sealing techniques include the application of a biogenic sealing material over the opening to seal the wound. However, proper placement of the sealing material is difficult to achieve and the plug of sealing material left inside the blood vessel may result in serious health risks to the patient.

As a result, devices have been developed which are inserted through the puncture in order to suture openings created in blood vessels. However, these devices suffer from various drawbacks.

For example, U.S. Pat. No. 5,417,699 to Klein et al. describes a device wherein two needles coupled to a distal end of an insertion shaft are surrounded by an outer sheath during insertion into a blood vessel. Once inside the blood vessel, the outer sheath is withdrawn and bowed sections of the needles, which had been constrained within the outer sheath against an outward spring bias, deploy away from the insertion shaft. The insertion shaft is then withdrawn drawing the needles through the walls of the internal structure. The arcuate shape of the needles is intended to bring the needles back along a curved path toward the insertion shaft so that the free ends of the needles may be captured on the shaft and the device withdrawn from the body. Thereafter, the distal ends of the needles must be detached from the insertion shaft so that a length of suture extending between distal ends of the two needles may be drawn through the walls of the internal structure to seal the opening.

However, the curved shape of the proximal ends of the needles of this device requires an insertion sheath of increased diameter. Thus, after withdrawal of a treatment catheter from an opening formed in an internal structure, insertion of the increased diameter outer sheath of the device of Klein et al. actually expands the opening in the wall of the internal structure. In addition, the device of Klein et al. employs several slidably mounted concentric shafts and mechanisms for the deployment and capture of the needles which make the device costly to manufacture and cumbersome to operate.

SUMMARY OF THE INVENTION

The present invention is directed to a device for sealing an opening in an anatomical structure within a living body. The device includes a tube including a proximal portion extending along an axis coupled to a distal portion extending along the axis by a central portion, wherein the central portion extends away from the axis to form a gap between a distal end of the proximal portion and a proximal end of the distal portion. The tube may be made of a flexible material, or may have portions, such as the distal portion, which are flexible. A needle retention channel formed within the distal portion for holding a plurality of needles therein extends along the axis to an opening formed in the proximal end of the distal portion. In addition, a needle receiving channel formed within the proximal portion extends along the axis to an opening formed in the distal end of the proximal portion. Finally, a lumen extends from an opening formed in the end of the proximal portion to the needle retention channel. Thus, when the device is in an operative position, the tube extends through the opening in the anatomical structure with the opening in the distal end of the proximal portion and the opening in the proximal portion on opposite sides of the anatomical structure.

The present invention is also directed to a method including the steps of guiding into an opening in an anatomical structure, a device including substantially linear proximal and distal portions extending along a common axis and a curved central portion coupling the proximal and distal portions so that a gap is formed therebetween. The device is positioned so that the curved central portion is within the opening with a needle retention channel opening on a distal side of the anatomical structure and a needle receiving channel opening on a proximal side of the anatomical structure. The doctor then draws a pull cord attached to a distal end of a first needle out to bring a first needle proximally out of the needle retention channel through the anatomical structure and through the needle receiving channel to bring a first end of the suture through the anatomical structure. Thereafter, the device is rotated to a second desired position so that a second portion of the anatomical structure adjacent to the opening is located within the gap and a pull cord attached to a distal end of a second needle is drawn to bring the second needle proximally out of the needle retention channel through the anatomical structure and into the needle receiving channel so that the second end of the suture is drawn through the anatomical structure. The first and second ends of the suture are then secured together to seal the opening.

A further embodiment of the invention is directed to a surgical stitching device comprising a flexible tube including substantially linear proximal and distal portions defining an axis and a curved central portion coupling the proximal and distal portions so that a gap is formed therebetween. A puncture needle channel extends through the proximal portion along the axis to an opening formed in the distal end of the proximal portion, while a puncture needle receiving channel extends through the distal portion along the axis to a suture retention channel of relatively larger cross-sectional area. A puncture needle including a central lumen is slidably received in the puncture needle channel so that, by applying pressure to a proximal end of the puncture needle, a user may manually move the puncture needle out of the opening formed in the distal end of the puncture needle channel, across the gap and into the puncture needle retention channel until a distal end of the puncture needle is received within the suture retention chamber. A piston is slidably received in the central lumen so that, when the distal end of the puncture needle is received within the suture retention chamber, a user may move the piston distally through the central lumen to release the contents of the central lumen into the suture retention chamber.

The present invention is further directed to a device for sealing an opening in an anatomical structure which includes a flexible tube having proximal and distal parts coupled together by a central part which extends away from the proximal part to form a gap between a distal end of the proximal part and a proximal end of the distal part and wherein the proximal part includes an end portion which, when the device is in an operative position, is located outside the body. The flexible tube includes a distal needle lumen extending within the distal part to a distal part opening formed in the proximal end of the distal part; a proximal needle lumen extending within the proximal part to a proximal part opening formed in the distal end of the proximal part so that the proximal part opening faces the distal part opening across the gap formed by the central part. The device also includes a proximal needle pusher slidably received within the proximal needle lumen for pushing a needle coupled to a length of suture distally through the proximal needle lumen, out of the proximal part opening and across the gap into the distal part opening so that, when the device is positioned with a first portion of the anatomical structure received within the gap, the needle pierces the first portion of the anatomical structure before entering the distal part opening. The device also includes a distal needle pusher slidably mounted within the distal needle lumen for pushing a needle proximally out of the distal part opening, across the gap and into the proximal part opening so that, when the device is positioned with a second portion of the anatomical structure received within the gap, the needle may pierce the second portion of the anatomical structure prior to entering the proximal part opening.

BRIEF DESCRIPTION OF THE DRAWINGS

FIG. 1 shows a side view of a cross-section of a suturing device according to a first embodiment of the invention;

FIG. 2 shows a top view of a cross-section of a suturing device according to the first embodiment of the invention;

FIG. 3A shows a cross-section of a device according to the first embodiment of the invention taken along line 3—3 of FIG. 1;

FIG. 3B shows an alternative cross-section of a device according to the first embodiment of the invention taken along line 3—3 of FIG. 1;

FIG. 4A shows a cross-section of a device according to the first embodiment of the invention taken along line 4—4 of FIG. 2;

FIG. 4B shows an alternative cross-section of a device according to the first embodiment of the invention taken along line 4—4 of FIG. 2;

FIG. 5 shows a partially cross-sectional view of a blood vessel within a body with a guide wire inserted therein;

FIG. 6A shows a partially cross-sectional view of the blood vessel with a device according to the first embodiment of the present invention received on the guide wire in a first desired position;

FIG. 6B shows a partially cross-sectional view of the blood vessel with the device as shown in FIG. 6A wherein a needle has been drawn through the body tissue received in the central gap;

FIG. 7 shows a partially cross-sectional view of the blood vessel with a device according to the first embodiment of the present invention in a second desired position;

FIG. 8 shows a partially cross-sectional view of the blood vessel with a device according to the first embodiment of the present invention partially removed from the blood vessel;

FIG. 11 shows a side view of a cross-section of a suturing device according to a second embodiment of the invention;

FIG. 12 shows a cross-section of a device according to the second embodiment of the invention taken along line 12—12 of FIG. 11;

FIG. 13 shows a cross-sectional view of a puncture needle according to the second embodiment of the present invention;

FIG. 14 shows a side view of a plunger according to the second embodiment of the present invention;

FIG. 23 shows a sketch of a needle anchor for use with the fifth embodiment of the present invention;

FIG. 24 shows a cross section of the proximal end of the main body of the device of FIG. 22;

FIG. 28 shows a side cross-sectional view of a suturing device according to a sixth embodiment of the invention;

FIG. 29 shows a cross section of the device of FIG. 28 through line C—C;

FIG. 30 shows a cross section of the device of FIG. 28 through line B—B;

FIG. 31 shows a cross section of the device of FIG. 28 through line A—A;

FIG. 41 shows a cross-section of the device of FIG. 40 taken along line A—A;

FIG. 42 shows a push plate according to the present invention;

DETAILED DESCRIPTION OF THE INVENTION

Figure 9:
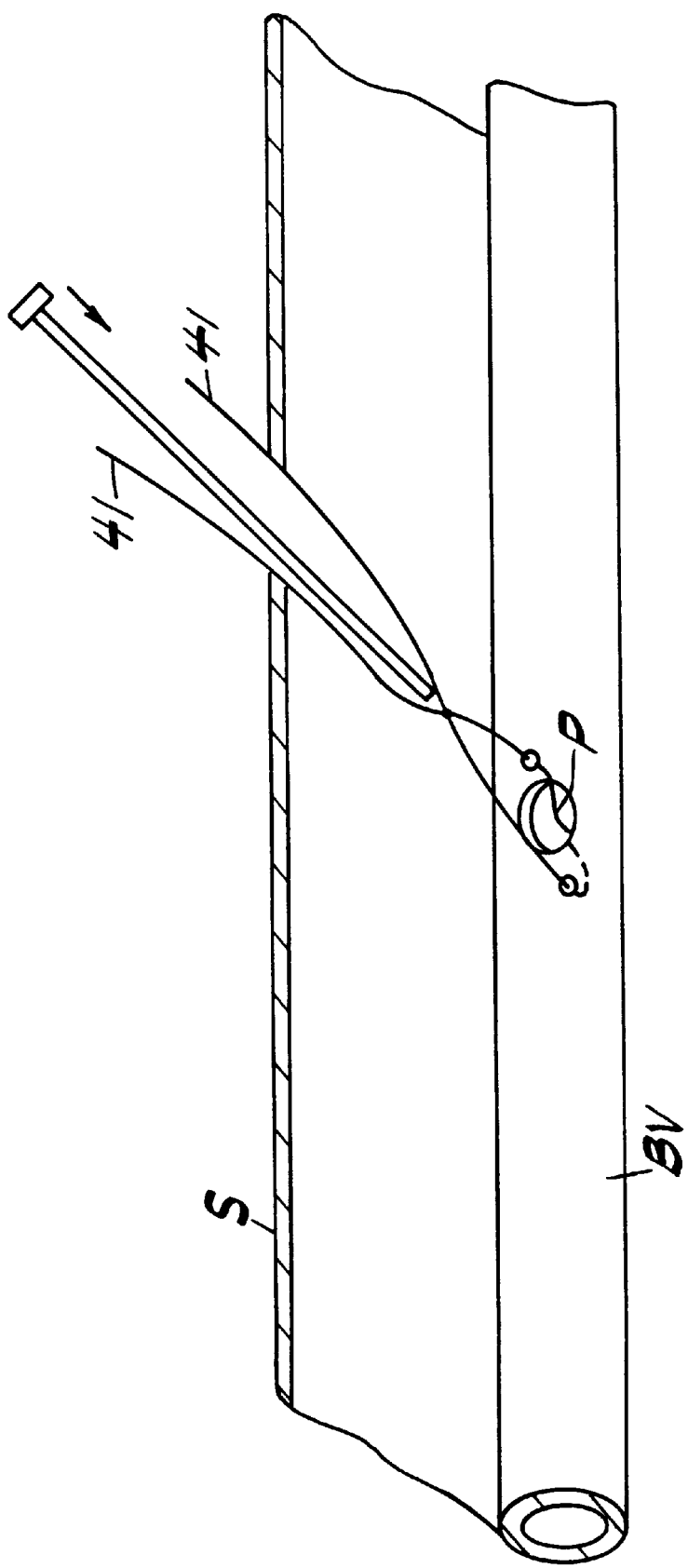
FIG. 9 shows a slip knot tied in a suture loop extending through the wall of the blood vessel being urged toward the blood vessel.

Referring now to the drawings, in which like reference numerals identify similar or identical elements, FIGS. 1–8 show a device 1 according to a first embodiment of the invention for suturing punctures in anatomical structures, such as blood vessels, internal organs and the like. The device 1 includes tube 16 of substantially circular cross-section, which has a proximal part 18 and a distal part 24. The proximal part 18 extends from a first end 20 through a central arcuate portion 22 to a second end 21 which mates with a proximal end 23 of the distal part 24. The central arcuate portion may preferably be substantially circular with a radius of from 0.100" to 0.600". The tube 16 is preferably constructed of a thermoplastic such as polyurethane, polyester, or the like, in two or three parts bonded together. The various parts of the tube 16 may preferably be either extruded or molded. The length of the tube 16 may be selected to fit the requirements of a particular situation and is preferably between 1" and 16" in length.

The tube 16 includes a large interior needle withdrawal lumen 26 which extends through the proximal part 18 from the first end 20 to an opening 10 at a proximal end of the central arcuate portion 22. As seen in FIGS. 3A and 3B, the needle withdrawal lumen 26 may preferably be oval in cross-section and may include an optional slot 28 opening to the outside of the tube 16.

In addition, a flash back lumen 30 extends from an opening 31 formed in the proximal part 18 through the central arcuate portion 22 to open into two needle retention bores 32 and 32' formed side-by-side in the distal part 24. As seen in FIG. 3A, the flash back lumen 30 may be circular in cross-section and is sized to simultaneously accommodate two strands of the suture 41 and the two pull cords 43 and 43'. However, as shown in FIG. 3B, the cross-section of the flash back lumen 30 may preferably include side-by-side hemispherical channels 45 and 45' for receiving the loop 41' of the suture 41 and the two pull cords 43 and 43'. This helps to ensure that the second needle 37' is not accidentally drawn out of the needle retention bore 32' when the first needle 37 is being pulled out. The needle retention bores 32 and 32' extend from distal ends to openings 33 and 33', respectively, formed at a position in the distal end of the central arcuate portion 22 opposite the opening 10. In addition, a substantially straight stiffening member may be inserted into the flash back lumen 30 in order to straighten the central arcuate portion 22 during insertion of the device 1 into the body. Alternatively, the device 1 may be made straight and, after insertion into the body, a curved stiffening member may be inserted to bend the device 1 thereby creating the central arcuate portion 22.

As seen in FIGS. 4A and 4B, the retention bores 32 and 32' have cross-sectional shapes including first portions 35, each shaped to receive a needle 37 or 37' respectively and second portions 39, each shaped to receive a suture 41 and pull cord 43 or 43' respectively. The first portions 35 are shaped to correspond to the cross-section of the needles 37 and 37' which in the preferred embodiment is substantially circular. The second portions 39, which are of reduced size so that the needles 37 and 37' are unable to enter, may be either rectangular or triangular projections extending from the first portions 35 and are sufficiently large to simultaneously accommodate the suture 41 and one of the pull cords 43 and 43'. The suture 41, which will preferably be in the range of 0.004" to 0.010" in diameter and from 15" to 35" in length, may be formed of either "reabsorbable" or "non-reabsorbable" material, as is well known in the art. The pull cords 43 and 43' will preferably be formed of non-reabsorbable material and will be of similar diameter to the suture 41. Those skilled in the art will recognize that the function of the pull cords 43 and 43' may be filled by a loop 41' of the suture 41 coupled between the distal ends of the needles 37 and 37' extended through the flash back lumen 30 so that, when the loop 41' of the suture 41 is extended proximally, the needles 37 and 37' are urged proximally through the needle retention bores 32 and 32'.

As the device 1 according to the first embodiment includes a single pair of needles, this device should preferably be used to close punctures of 9.0 French size and smaller (each French size representing 0.013" in diameter). The tube 16 will, therefore, preferably be 6.0 or 8.0 French size. As described below in reference to further embodiments of the invention, devices employing two or more pairs of needles 37 and 37' may be employed to close punctures larger than 9.0 French size. Each of the needles 37 and 37' may preferably be constructed of stainless steel, be between 2" and 8" in length and have a diameter between 0.010" and 0.030".

When the device 1 is in an operative configuration, the suture 41 extends between the distal ends of two needles 37 and 37' received in the needle retention bores 32 and 32'. In the first embodiment of the invention, optional pull cords 43, 43' extend from the distal end of each of the needles 37 and 37' through the second portions 39 of the needle retention bores 32 and 32', via the flash back lumen 30, to the opening 31. However, the suture 41 may, alternatively, extend from the distal ends of the needles 37 and 37' through the second portions 39 of the needle retention bores 32 and 32', via the flash back lumen 30, to the opening 31 so that a portion of the suture loop 41' which extends out from the opening 31 may provide the function of the pull cords 43 and 43', as described below.

Finally, a guide wire lumen 34 extends through the distal part 24 of the device 1 from a proximal opening 36 to a distal opening 38 formed in a second end 40 of the device 1.

In operation, as shown in FIGS. 5–10, when an invasive procedure is performed on a patient which requires the insertion of a catheter into a blood vessel (or other anatomical structure within the body), an introducer sheath is inserted through the skin (S) into the patient's body through a puncture (P) in a wall of the blood vessel (BV). A guide wire 44 is inserted through the puncture to a target area within the blood vessel and a catheter is inserted through the introducer sheath, along the guide wire 44, to a target area within the blood vessel. After the procedure is complete, the catheter and the introducer sheath are withdrawn and the guide wire 44 is left in place. A proximal end of the guide wire 44 is then inserted through the guide wire lumen 34 and the device 1 is inserted into the body and moved along the guide wire 44 through the puncture until the central arcuate portion 22 straddles a portion of the blood vessel wall adjacent to the puncture.

By observing the flash back lumen 30 and the needle withdrawal lumen 26, the doctor may determine when the device 1 is in the desired position. Specifically, when the device 1 is inserted far enough into the blood vessel, blood will be observed in the flash back lumen 30. However, if blood is observed in the needle withdrawal lumen 26, the doctor knows that the device 1 has been inserted too far into the blood vessel.

As the device 1 is inserted into the blood vessel, the distal part 24 of the tube 16 may bend so that the device 1 is received within, and extends in the direction of the blood vessel 90 without straining the blood vessel 90. In this position, the openings 33 and 33' are on the distal side of the puncture facing the opening 10 which is located on the proximal side of the puncture.

As shown in FIG. 6B, the doctor then rotates the device 1 into a desired orientation and draws the pull cord 43 out of the opening 31, thus drawing one of the needles 37 forward through the needle retention bore 32 so that a pointed, proximal end of the needle 37 is drawn through the wall of the blood vessel, enters the opening 10 and extends into the needle withdrawal lumen 26. The needle 37 is then withdrawn through the needle withdrawal lumen 26, drawing a first end of the suture 41 through the wall of the blood vessel and into the needle withdrawal lumen 26. The needle 37 is drawn forward by means of the pull cord 43 until a proximal end of the needle 37 protrudes from the proximal end of the needle withdrawal lumen 26. The proximal end of the needle 37 is then grasped by the doctor and withdrawn from the needle withdrawal lumen 26. In order to ensure that the needles 37 and 37' will extend through the needle withdrawal lumen 26, the needles 37 and 37' will preferably be at least 4" in length.

Thereafter, the doctor rotates the device 1, as shown in FIG. 7, until the central arcuate portion 22 straddles the blood vessel wall in a desired position relative to the point at which the first end of the suture 41 penetrated the blood vessel wall. Those skilled in the art will understand that this "desired position" will usually be on the opposite side of the puncture, so that the device 1 will be rotated approximately 180° after the first needle 37 is withdrawn. When the device 1 is in the second desired orientation, the doctor draws the pull cord 43' out of the opening 31 thereby urging the second needle 37 forward through the needle retention bore 32' so that the pointed, proximal end of the second needle 37 is drawn through the wall of the blood vessel, enters the opening 10 and extends into the needle withdrawal lumen 26. The second needle 37 is withdrawn through the needle withdrawal lumen 26, drawing the second end of the suture 41 through the wall of the blood vessel and into the needle withdrawal lumen 26 as described above.

Figure 10:
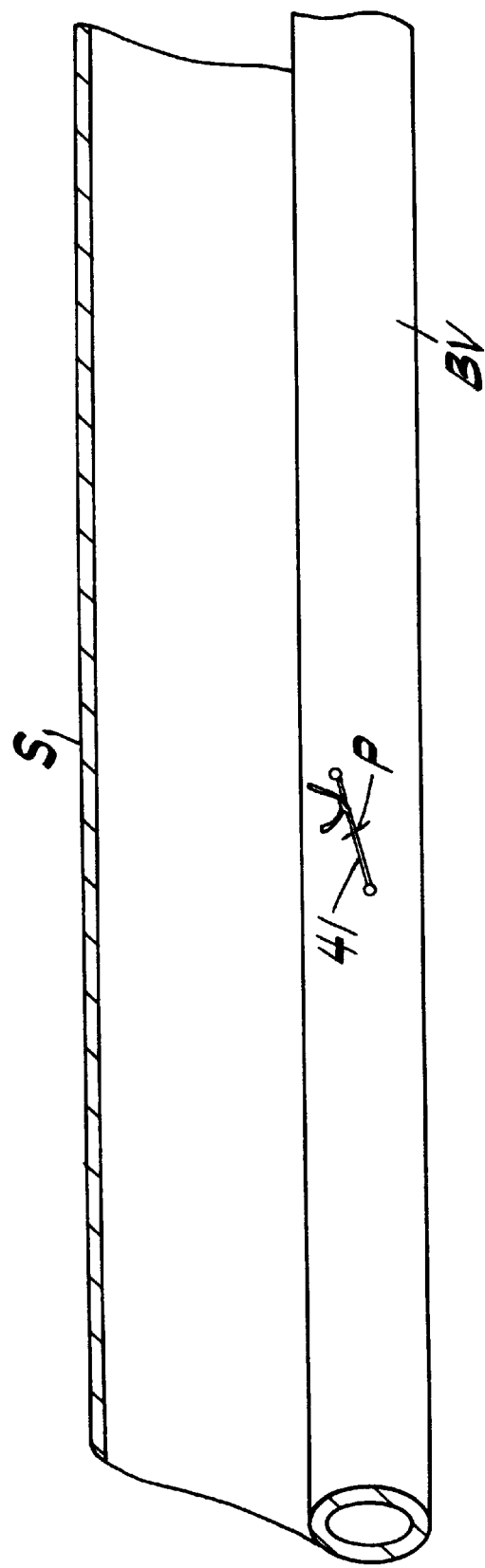
FIG. 10 shows a suture sealing the puncture.
Figure 15:
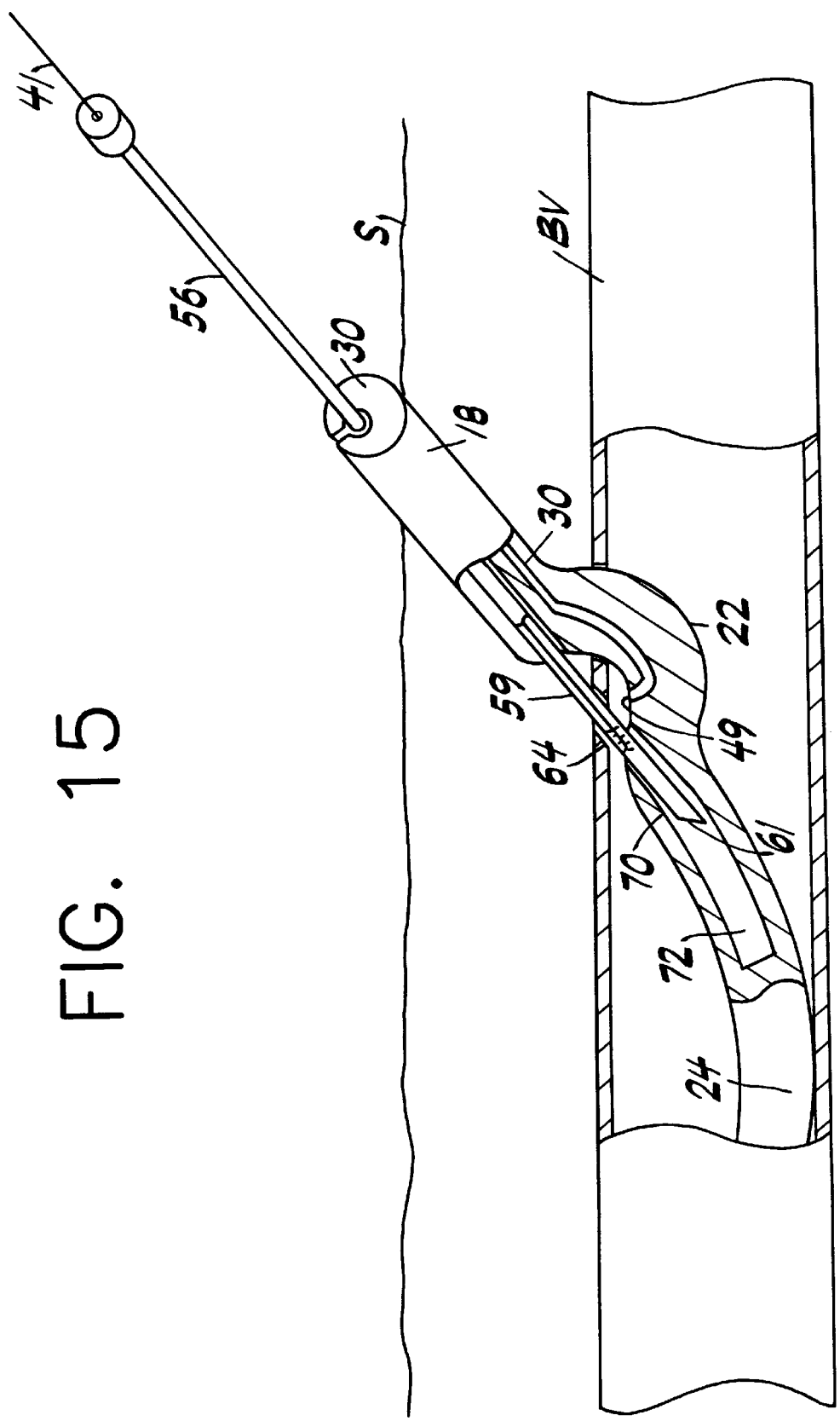
FIG. 15 shows a partially cross-sectional view of the blood vessel with a device according to the second embodiment of the present invention in a first desired position.
Figure 16:
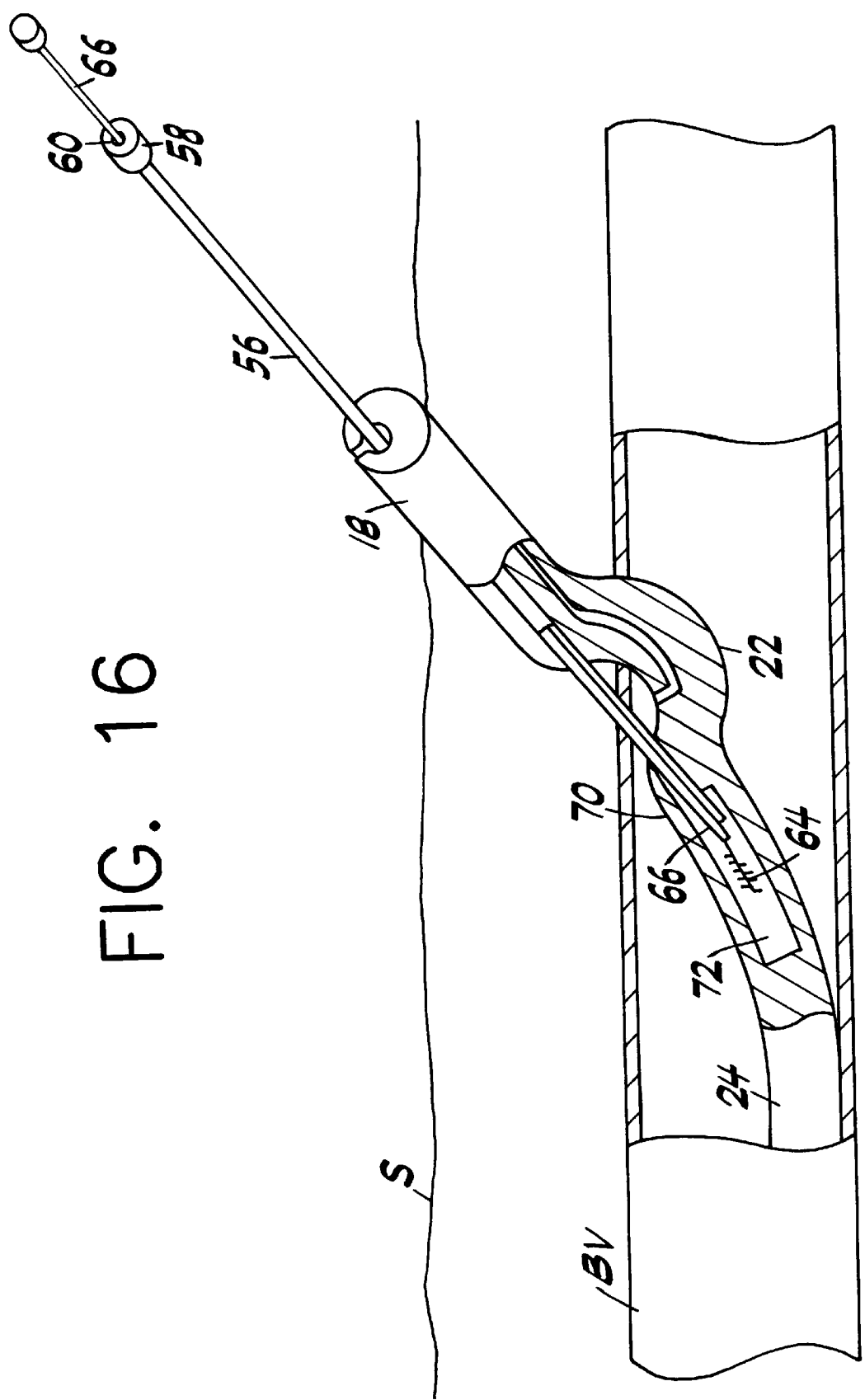
FIG. 16 shows a partially cross-sectional view of the blood vessel with a device according to the second embodiment of the present invention in the first desired position where a suture has been passed through the wall of the blood vessel and introduced into a suture retention chamber.

As shown in FIGS. 8–10, the doctor withdraws the device 1 from the body and detaches the suture 41 from the ends of the needles 37 and 37' and ties the two ends together in a slip knot which is urged inward toward the blood vessel and drawn tight in order to seal the puncture. Of course, those skilled in the art will appreciate that, once the two ends of the suture 41 have been drawn through the blood vessel wall, various other methods of fastening the two ends together may be employed.

FIGS. 11–19 show a suturing device according to a second embodiment of the present invention. The tube 16 of the device 1' according to the second embodiment is preferably similar in size and flexibility to the device 1 of the first embodiment and differs only as described below. In addition, those skilled in the art will recognize that, except where specifically stated, each of the variations described above in reference to the first embodiment may also be applied to all other embodiments.

As seen in FIG. 12, the cross-section of the proximal part 18 of the device 1' shows a flash back lumen 30 of circular cross-section. The flash back lumen 30 of this embodiment extends from the first end 20, through the proximal part 18 to an opening 49 formed adjacent to the opening 68.

In addition, instead of the needle withdrawal lumen 26 of the first embodiment, the proximal part 18 of the device 1' includes a substantially circular puncture needle channel 50 extending from the first end 20 of the device 1' to an opening 52 at a proximal end of the central arcuate portion 22. This puncture needle channel 50 is also shown including an optional slot 54 extending through the surface of the tube 16 along the length of the puncture needle channel 50.

A puncture needle 56, having an increased diameter gripping surface 58 at a proximal end, is slidably received in the puncture needle channel 50. The puncture needle 56 includes a central channel 59 extending from an opening 60 formed in the gripping surface 58 to an opening 61 formed in a distal end 62 of the puncture needle 50. One suture 41, integrally formed with or coupled to a respective anchor member 64, is received within the central channel 59. The anchor member 64 may be constructed as a coiled stainless steel spring.

Those skilled in the art will recognize that, if the puncture needle 56 is provided with a slot extending from a proximal end to a distal end thereof, a suture loop 41' may be formed with a single suture 41 having anchor members 64 at both ends. That is, after a first end of the suture has been inserted into the suture retention chamber 72, a first length of this suture 41 may be drawn out through the slot and a second anchor member 64 attached to a second end of the suture 41 may be inserted into the suture retention chamber 72 through a second portion of the blood vessel wall as described above. Thereafter, the device 1' is withdrawn from the body and the two ends of the suture loop 41' are tied together and, using known techniques, the knot is maneuvered so that it ends up on the outside of the blood vessel.

A plunger 66 is slidably received within the central channel 59 so that the anchor member 64 is located between the opening 61 and a distal end of the plunger 66 so that, when the plunger 66 is urged distally into the central channel 59, the anchor member 64 is moved toward the opening 61.

An opening 68 opposite the opening 52 at a distal end of the central arcuate portion 22, extends through a needle reception slot 70 to a suture retention chamber 72 which has an increased diameter relative to the needle reception slot 70. Those skilled in the art will recognize that many variations may be made to the structure of the anchor member 64 so long as sufficient stiffness is maintained and the anchor member is dimensioned so as to prevent the suture 41 from being withdrawn from the suture retention chamber 72 during withdrawal of the device 1' from the body.

In operation as shown in FIGS. 15–19, the device 1' is positioned with the central arcuate portion 22 straddling the blood vessel wall with the openings 52 and 68 on opposite sides of the wall (proximal and distal, respectively) and rotated to a desired position as described above in regard to the device 1 of the first embodiment.

As described above in regard to the device 1, the flash back lumen 30 may be used to determine whether or not the device 1' is in the desired position. Specifically when the device 1' is in the desired position, blood should be observed only in the flash back lumen 30, not in the needle channel 50. Blood in the needle channel 50 indicates that the device 1' has been advanced too far into the blood vessel. That is, blood in the needle channel 50 indicates that the opening 52 is improperly positioned within the blood vessel. When the device 1' is properly positioned, the doctor presses upon the gripping surface 58 to urge the a sharp, distal end of the puncture needle 56 distally out of the opening 52, through the wall of the blood vessel and into the opening 56.

When the puncture needle 56 has been inserted into the suture retention chamber 72, the doctor pushes the plunger 66 distally within the central channel 59 to release the anchor member 64 into the suture retention chamber 72. The puncture needle 56 is then withdrawn from the suture retention chamber 72 and the plunger 66 is completely withdrawn from the central channel 59.

Where the device 1' includes the optional slot 54, the suture 41 may then be withdrawn from the puncture needle channel 50 through the slot 54. This allows the diameter of the puncture needle channel 50 to be minimized while providing sufficient room for the puncture needle 56 to pass therethrough. Then a second anchor member 64 and a second suture 41 are inserted into the central channel 59.

Figure 17:
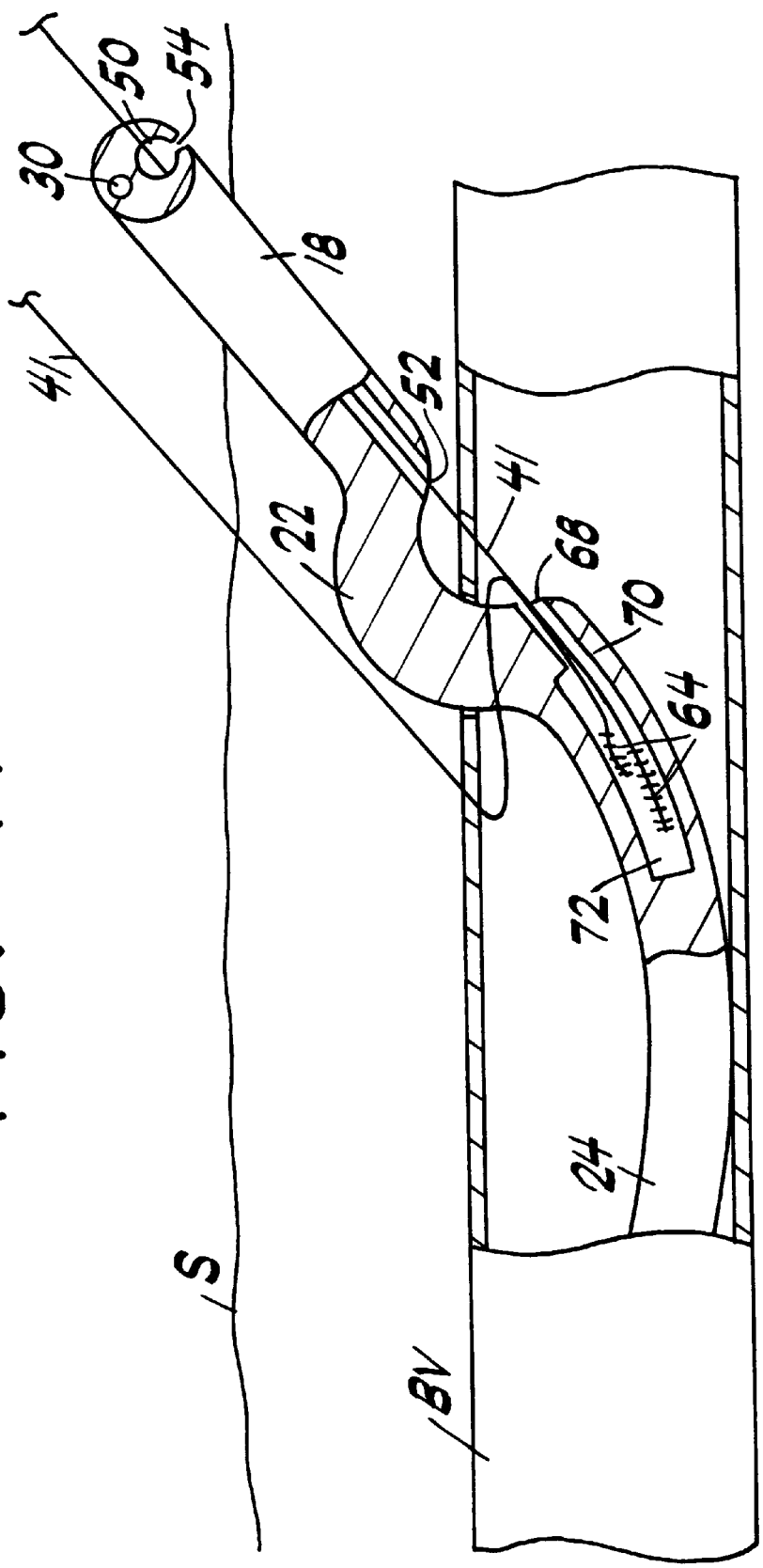
FIG. 17 shows a partially cross-sectional view of the blood vessel with a device according to the second embodiment of the present invention in a second desired position.

As shown in FIG. 17, the doctor then reorients the device 1' into the second desired position, as described above in regard to the first embodiment, the doctor presses upon gripping the surface 58 to urge the sharp, distal end of the puncture needle 56 distally out of the opening 52, through the wall of the blood vessel and into the opening 56 so that the opening 61 is within the suture retention chamber 72. Thereafter, the doctor inserts the plunger 66 into the central channel 59 and pushes it forward to release the anchor member 64 and the second suture 41 into the suture retention chamber 72. Those skilled in the art will understand that, instead of inserting a second suture 41 at this point, a gripping device may be introduced through the central channel 59 into the suture retention chamber 72 to grab and retrieve the anchor member 64 and draw it out through the central channel 59. This allows for the formation of a suture loop 41' without the need to knot two separate strands of suture 41 together.

Figure 18:
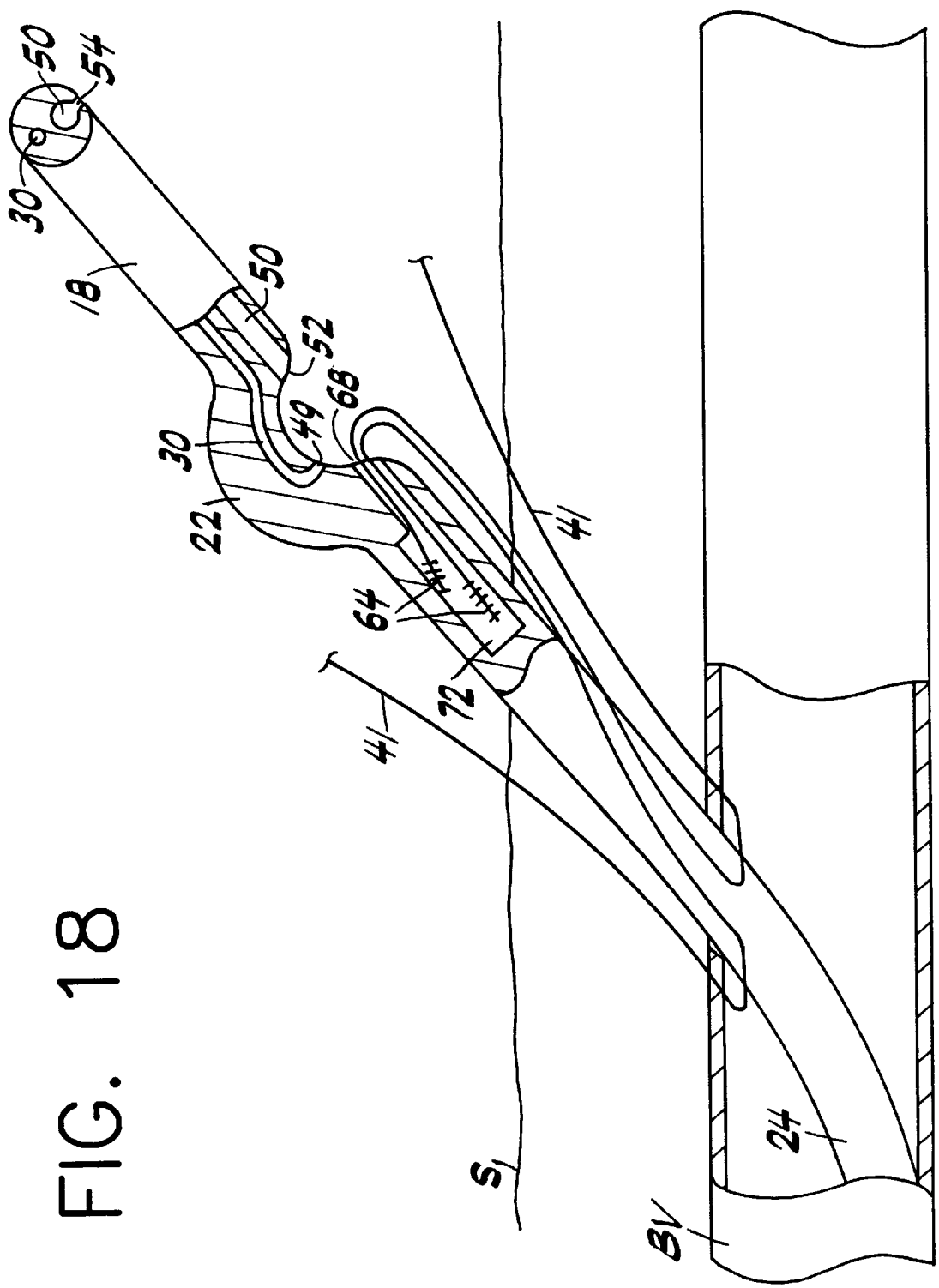
FIG. 18 shows a partially cross-sectional view of the blood vessel wherein the device according to the second embodiment has been partially withdrawn from the blood vessel.
Figure 19:
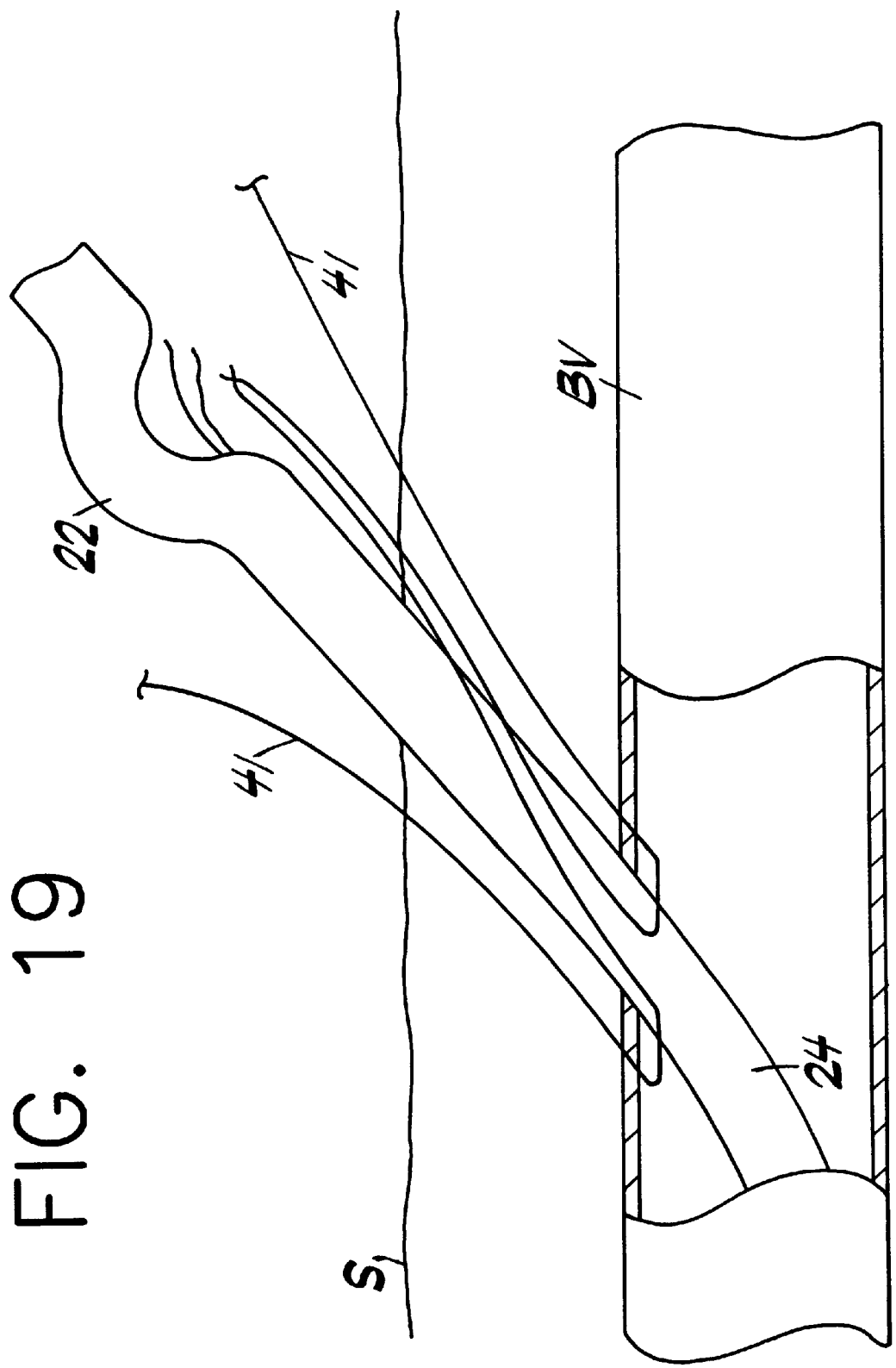
FIG. 19 shows a partially cross-sectional view of the blood vessel wherein the sutures have been severed from the anchor members and tied together.

The doctor then withdraws the device 1' from the body, as shown in FIG. 18, so that the ends of the sutures 41 extending from the opening 68 may be cut to release the sutures from the anchor members 64. Then, as shown in FIG. 19, these ends of the sutures 41 are tied together and the other ends are knotted together and tightened to seal the puncture.

Those skilled in the art will understand that, for larger punctures, the device 1' may be used to insert as many sutures 41 as are required to seal the puncture. Specifically, in order to close punctures larger than size 9.0 French, a single suture 41 may not be sufficient. Therefore, instead of using the device 1' as described above to insert two sutures 41 approximately 180° apart, a doctor may, for example, insert four sutures 41 at 90° intervals using the technique described above. Then, when the device 1' has been withdrawn from the body, the doctor must knot together a first pair of sutures 41 which are separated by approximately 180° and then knot the second pair. The two pairs of sutures 41 may be distinguished by color coding or any similar technique.

Figure 20:
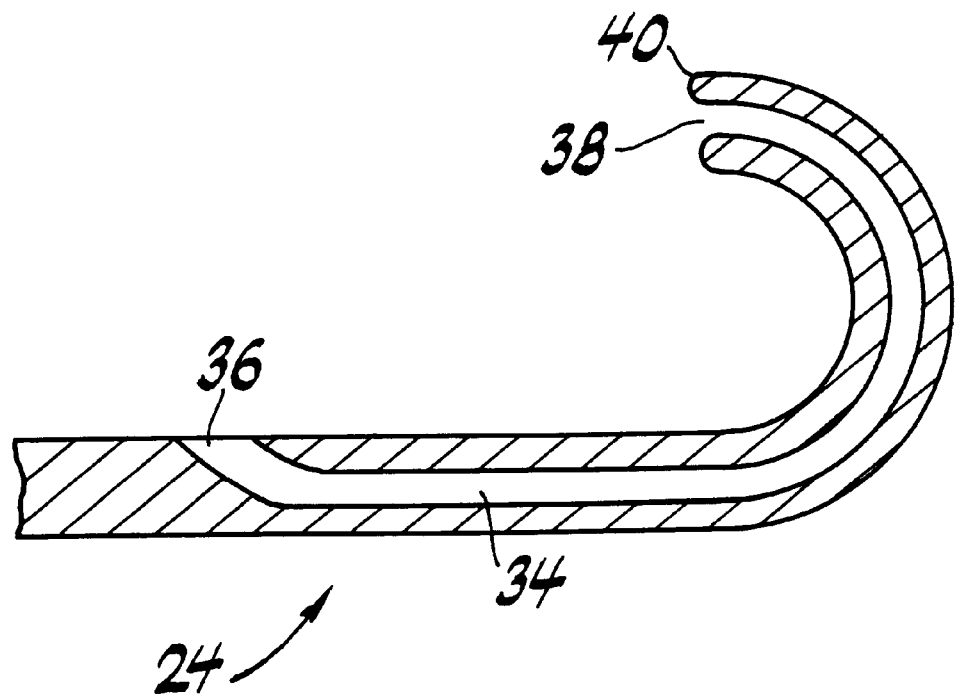
FIG. 20 shows a side view of a cross-section of a distal portion of a suturing device according to a third embodiment of the present invention.

A device 1" according to a third embodiment of the present invention is shown in FIG. 20. Aside from a modified distal part 24 as described below, the construction and operation of the device 1" is substantially identical to either of the first and second embodiments.

Specifically, the distal part 24 of the device 1" is constructed so that it has enhanced flexibility relative to the proximal part 18. In addition, the distal part 24 is biased so that, when in an unstressed state, it is "J" shaped—that is, the distal part 24 is curved so that the distal opening 38 formed in the second end 40 faces proximally. This facilitates insertion of the device 1" so that it contacts an inner wall of the blood vessel without damaging it. Specifically, the flexibility and "J" shape of the second end 40 allows the second end 40 to deflect away from the blood vessel's lining without penetrating or damaging the lining thereof. Of course, when received on the guide wire 44, the "J" shape of the distal part 24 will be less pronounced. However, the bias will maintain a slight curvature of the second end 40 deflecting the impact of the device 1" from the inside lining of the blood vessel.

Figure 21:
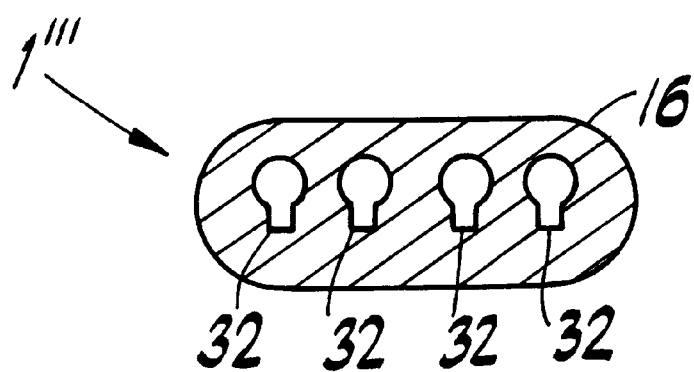
FIG. 21 shows a cross-section of a distal portion of a device according to the fourth embodiment of the invention.

As described above, in order to close punctures larger than size 9.0 French, a single suture 41 may not be sufficient. Thus, as shown in FIG. 21, a device 1''' according to a fourth embodiment of the invention may receive four needles 37 arranged side-by-side in four needle retention bores 32 formed in a tube 16 of substantially oval cross-section. Other than the oval cross-section and the provision of four needles, the construction and operation of the device 1''' is similar to that of the device 1 according to the first embodiment.

The oval cross section increases the stiffness of the device 1''' in the plane in which the four needles lie side-by-side, while retaining flexibility to bend perpendicularly to that plane. The four needles 37 of the device 1''' are coupled together in pairs and each pair of needles will be positioned so that the needles 37 of each pair penetrate the wall of the blood vessel on opposite sides of the puncture (approximately 180° apart). When the device 1''' has been removed from the body, each pair is then knotted together and the two knots are tightened to seal the puncture.

Of course, those skilled in the art will understand that each of the variations of the device 1 according to the first embodiment may also be applied to the device 1'''. Similarly, those skilled in the art will recognize that four needles 37 may be received in a device 1''' having two needle retention bores 32, each being of a length sufficient to hold two needles 37 arranged in series end-to-end.

Figure 22:
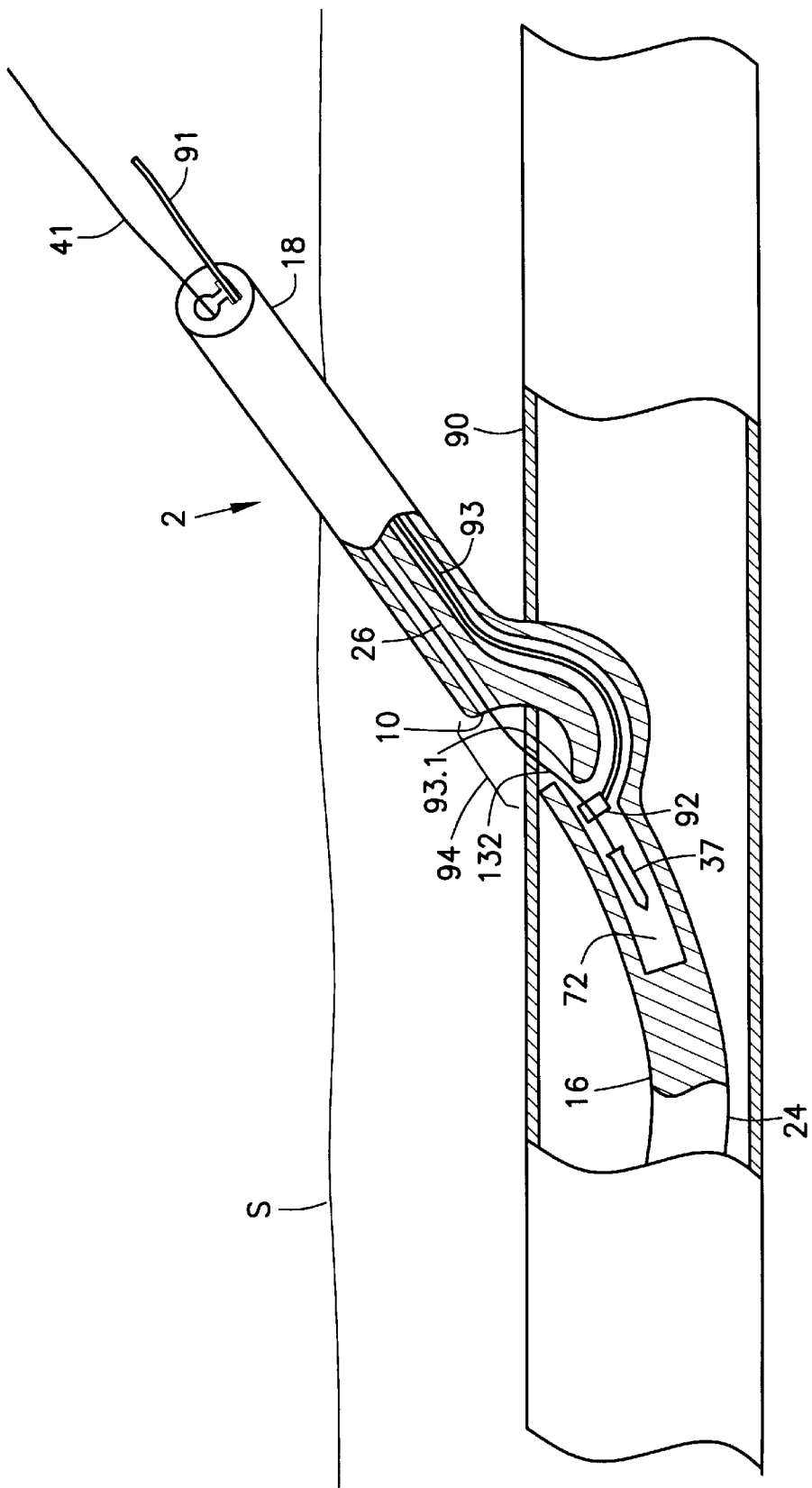
FIG. 22 shows a cross section of a suturing device according to a fifth embodiment of the invention.

FIG. 22 shows a further embodiment of the present invention which provides for placing multiple suture loops with a single needle 37 and a suture 41. The device 2 is substantially similar to the embodiments discussed above, with the common elements being identified by the same reference numbers.

The distal part 24 has a distal needle lumen 132 extending distally through the distal part 24 from an opening 93.1. As shown in FIG. 22, distal needle lumen 132 may optionally include a retention chamber 72. Alternatively, the device 2 may be formed with a distal needle lumen 132 of sufficient length so that the needle 37 may be advanced into the lumen 132 until a proximal end of the needle 37 has completely passed through the blood vessel wall.

The proximal part 18 of the main body 16 has a proximal needle lumen 26 and an anchor retrieval lumen 93 extending therethrough to distal opening 93.1. Of course, those skilled in the art will understand that the anchor retrieval lumen 93 may alternatively extend through at least a portion of the central arcuate portion 22 as, for example, does the flash back lumen 30 shown in FIG. 1. This would allow the needle retrieval lumen to also serve the same function as the flash back lumen 30 of the previously described embodiments. As shown in FIG. 24, the proximal needle lumen 26 and the anchor retrieval lumen 93 may preferably be joined by a slot 94 that runs at least the length of the proximal part 18 of the main body 16. The slot 94, which permits communication between the two lumens 26 and 93, allows the suture 41 to move from the proximal needle lumen 26 to the anchor retrieval lumen 93. Preferably, as the anchor retrieval lumen 93 extends through the central arcuate section 22, the slot 94 extends through the arcuate section 22 also, thereby connecting the anchor retrieval lumen 93 to the outside of the device 2 throughout the arcuate section 22. Such a construction allows the suture 41 to pass out of the anchor retrieval lumen 93 so that the device 2 may be removed from the suture 41 thus permitting the suture 41 to be knotted to seal the hole in the blood vessel 90.

As shown in FIG. 23, a flexible needle anchor 91 including a loop 92 formed on a distal end thereof is adapted to be slidably received in the needle retrieval lumen 93. The loop 92 is preferably biased so that, when in an unstressed state, a diameter of the loop extends at an angle relative to the axis of the needle anchor 91. The needle anchor 91 may include, for example, a marking or notch on the proximal end thereof, which corresponds with the orientation of the loop 92, thus assisting the user in properly positioning the needle anchor 91. The needle anchor 91 is preferably longer than the proximal part 18 of the main body 16 so that it may extend through the needle retrieval lumen 93 while remaining accessible to the user at the proximal end of the main body 16 and is more preferably at least long enough to extend through the needle retrieval lumen 93, across the gap 94, to a location adjacent to an opening 93.1 of the distal needle lumen 132.

Figure 25:
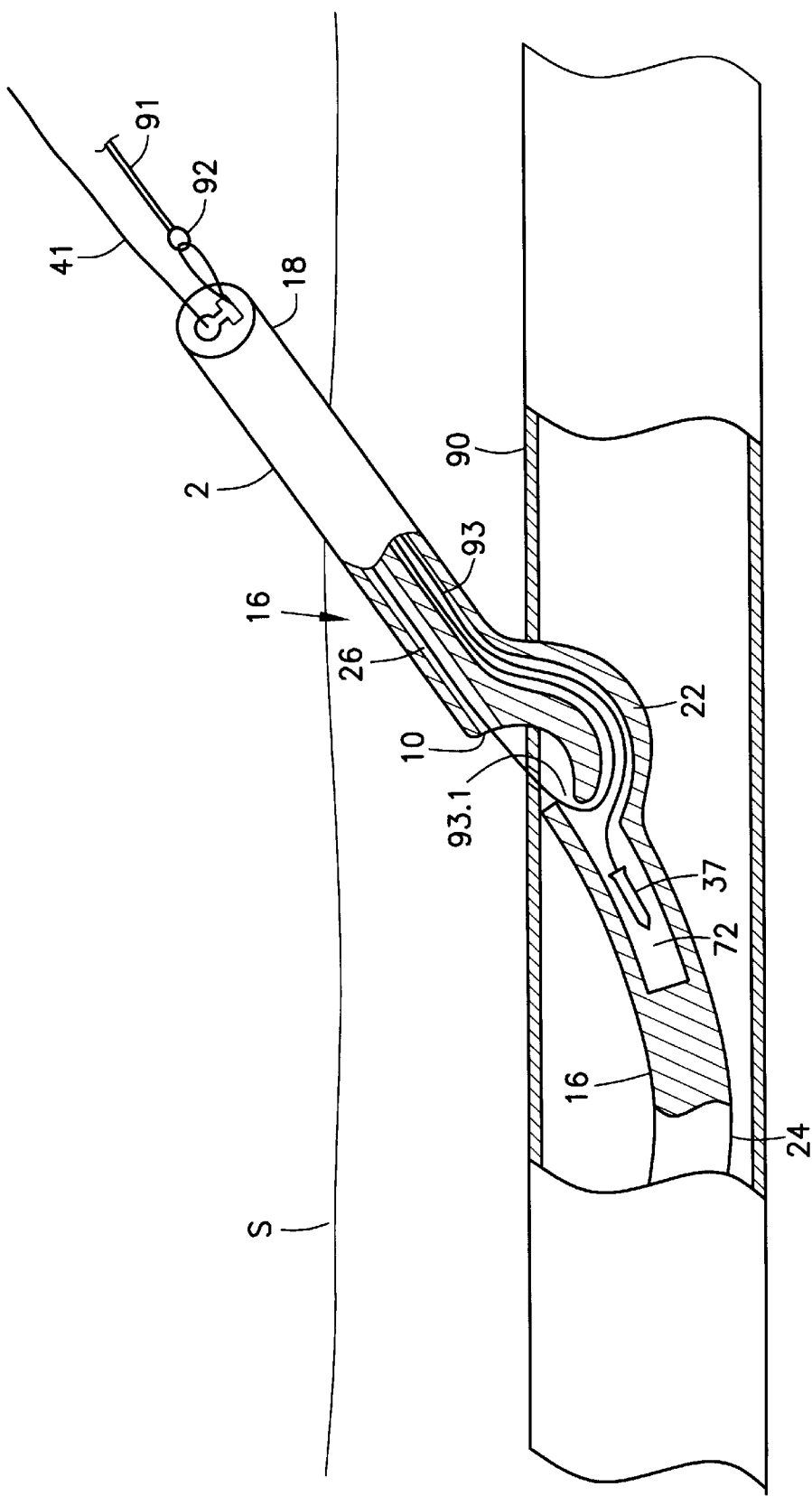
FIG. 25 shows the device of FIG. 22 wherein the anchor member has been withdrawn from the device to draw a loop of suture therefrom.
Figure 26:
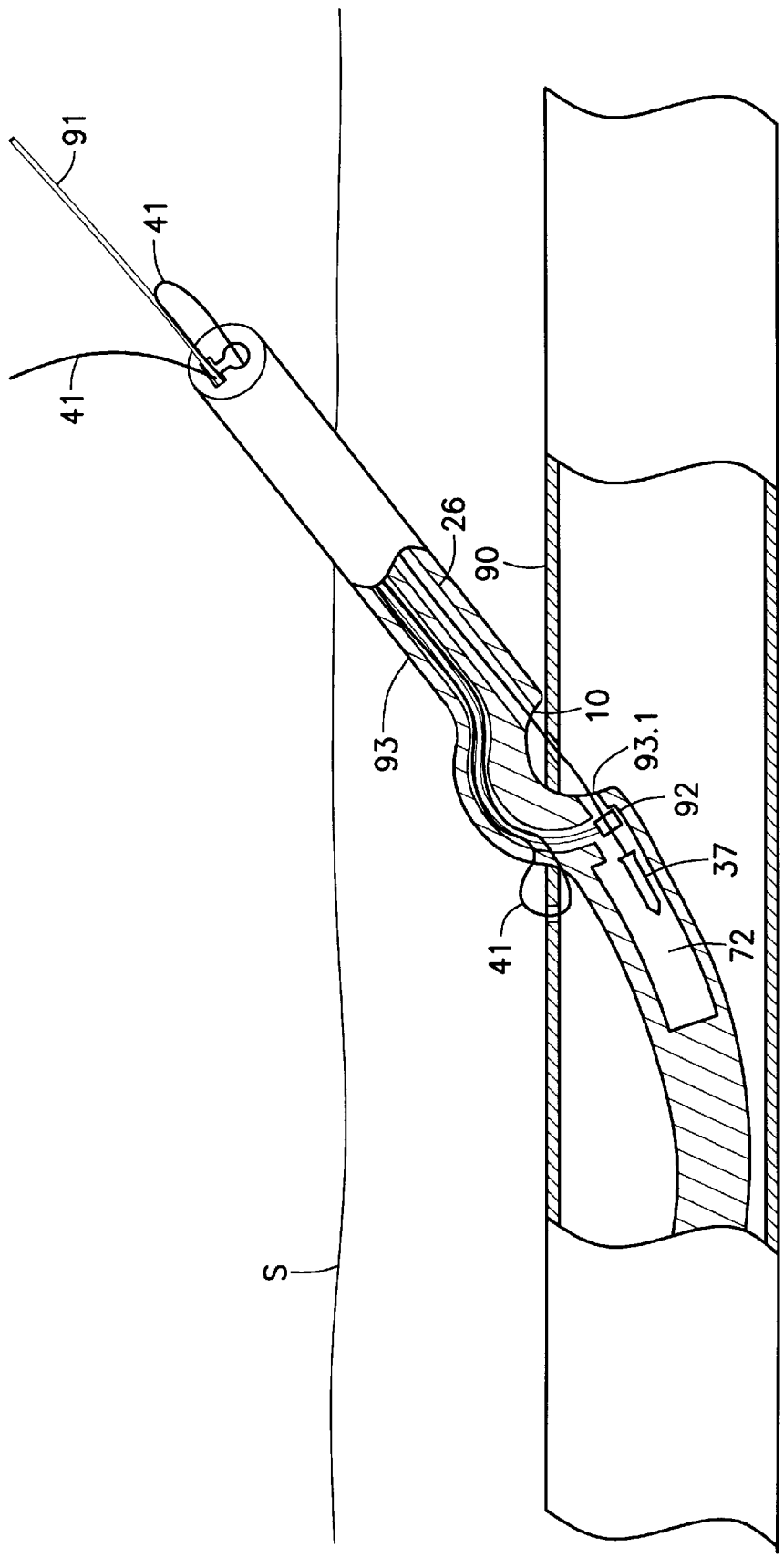
FIG. 26 shows the device of FIG. 22 wherein the needle has been reinserted at a second location.

In operation, as described above, the device 2 is placed within a living body so that the central arcuate portion 22 of the main body 16 extends through the hole formed in the blood vessel, with the distal part 16 located inside the blood vessel and the proximal part 18 outside the blood vessel. The needle anchor 91 is then slid through the anchor retrieval lumen 93 to the opening 93.1. Those skilled in the art will understand that the loop 92 need not be located directly inside the opening 93.1. Rather, it is necessary only that the loop 92 be positioned inside the blood vessel wall in alignment with the opening 10 and the opening 93.1 so that a needle 37 will pass therethrough. With the needle anchor 91 in place, a needle 37 is inserted through the proximal needle lumen 26 until it exits opening 10, passes through the portion of the blood vessel wall received within the gap 94, and passes through the loop 92 and into the distal needle lumen 132 via the opening 93.1. After the full length of the needle 37 has been placed through the blood vessel wall 90 in this manner, the needle anchor 91 is withdrawn through the needle retrieval lumen 93 to draw the suture 41 through the needle retrieval lumen 93 to the outside of the body, as shown in FIG. 25. The user may then withdraw the needle 37 by, for example, pulling the suture 41 so that the end of the suture 41 that is attached to the needle 37 is withdraw from the anchor retrieval lumen 93, thus withdrawing the needle 37.

The device may then be repositioned so that the gap 94 straddles a second portion of the blood vessel wall (e.g. a portion of the blood vessel wall that is on a different side of the hole from where the first suture was placed). The needle anchor 91 is then reinserted through the anchor retrieval lumen 93 so that the loop 92 is again positioned in alignment with the openings 10 and 93.1. The needle 37, preferably coupled to the same length of suture 41, is re-inserted through the proximal needle lumen 26 to pierce the second portion of the blood vessel wall, pass through the loop 92 and enter the distal needle lumen 132. The needle anchor 91 is again withdrawn through the anchor retrieval lumen 93 to withdraw a loop of the suture 41 along with it. The user then withdraws the needle 37 by again pulling the corresponding end of the suture 41. The user thereby creates a suture loop extending through the blood vessel wall at 2 locations separated by any angle desired by the user (180°, for example). This procedure may be repeated any number of times in order to place the single loop of the suture 41 through the blood vessel wall multiple times at a corresponding number of locations spaced around the circumference of the hole in the blood vessel wall at any orientations desired by the user. Alternatively, a separate length of suture 41 may be inserted with each rotation of the device 2, or with each two rotations, and the ends of the lengths of the suture 41 may later be connected together to form suture loops to seal the opening in the blood vessel wall. After placing the desired number of loops of the suture 41 through the hole in the blood vessel wall, the device 2 is removed from the puncture site.

Figure 27:
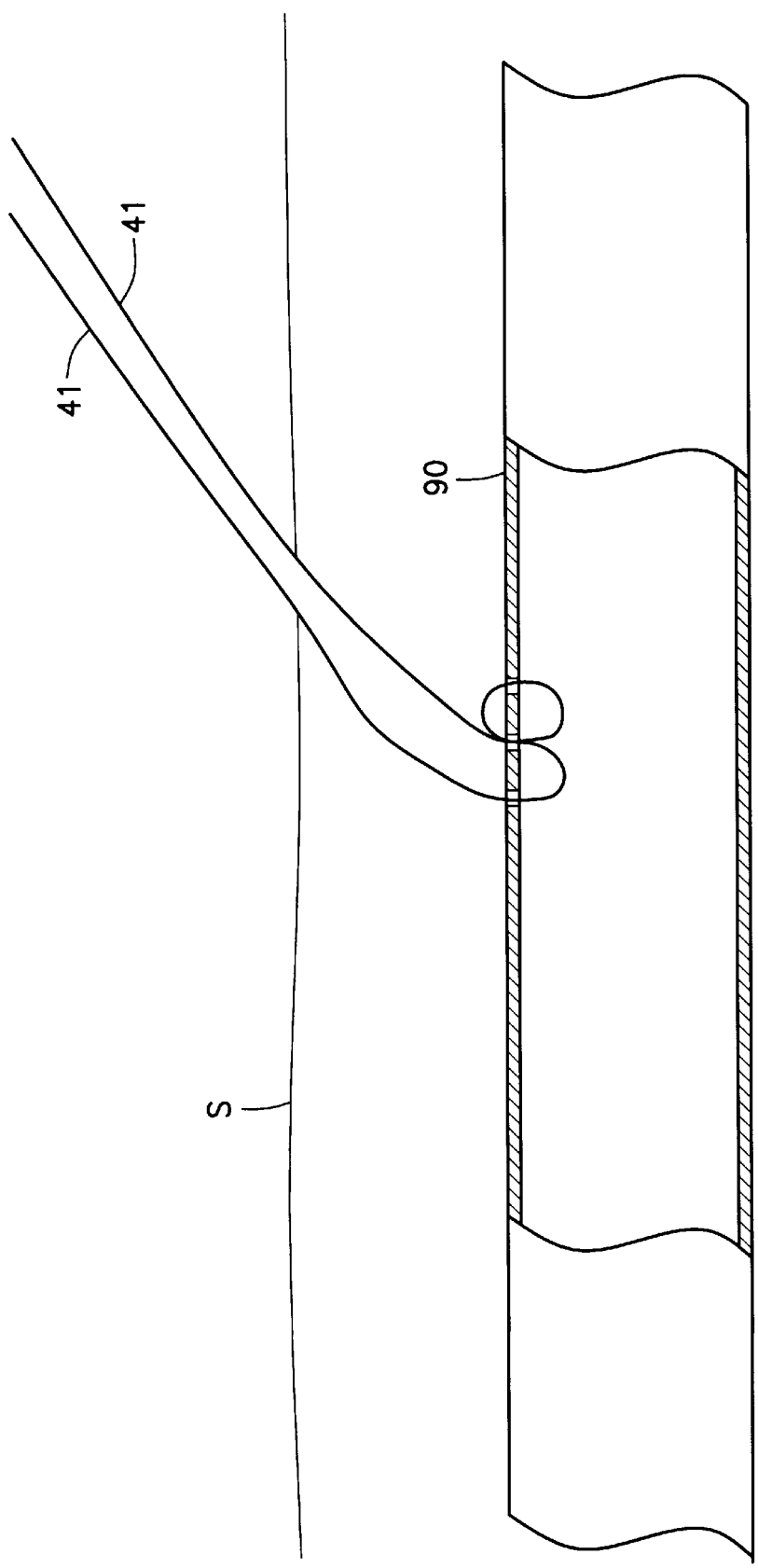
FIG. 27 shows the suture loop of FIG. 26 after the device has been withdrawn from the body.

The suture 41 may be removed from the device 2 as the loops of the suture 41 may pass through the slot 94 that connects the proximal needle lumen 26 and the anchor retrieval lumen 93. FIG. 27 shows an exemplary path of the suture 41 through the blood vessel according to this embodiment of the invention. The ends of the suture 41 may then be knotted to close the opening in the blood vessel wall.

Figure 35:
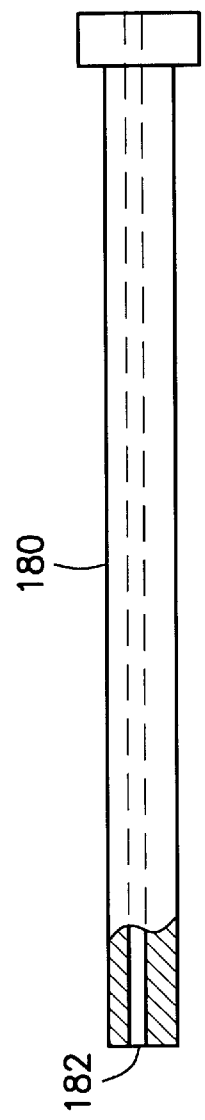
FIG. 35 shows a proximal needle pusher according to the sixth embodiment of the present invention.
Figure 36:
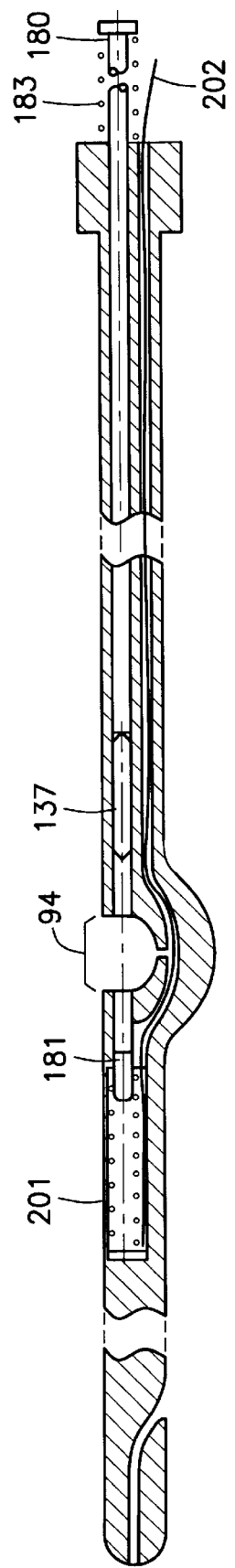
FIG. 36 shows a the device of FIG. 28 with the distal and proximal needle pushers of FIGS. 32 and 35, and the needle and suture of FIG. 34.

FIG. 28 shows a further embodiment of the present invention designated generally as device 100. Device 100 has features and operation similar to those of the previously discussed embodiments. However, the proximal needle lumen 126, which extends substantially through the length of the proximal part 118, is adapted to slidably receive therein a proximal needle pusher 180, shown in FIG. 35. The proximal needle pusher 180 is preferably a piston-like tubular member of sufficient length to push a needle 137 through the proximal needle lumen 126, across the gap 94, and into the distal needle lumen 132. As shown in FIGS. 35 and 36, a bore 182 extends through the proximal needle pusher 180, through which the suture 41 may pass. Also shown in FIG. 36, a biasing spring 183 may optionally be placed between the proximal needle pusher 180 and the main body 116 to bias the proximal needle pusher 180 to a neutral position in which a distal end of the needle pusher 180 is received within the proximal needle lumen 126. Thus, the biasing spring 183 operates to return the proximal needle pusher 180 to the neutral position.

As shown in FIGS. 28 and 31, the proximal part 116 may also contain a flashback lumen 130 and a cable lumen 203. The flashback lumen 130 provides fluid communication between its entry port 149 in the arcuate section 122 and its exit port 131 located, for example, at the proximal end of the proximal part 118. As with the previously described embodiments, the flashback lumen 130 allows the user to determine when the device 100 is in the desired position within the hole in the blood vessel. The cable lumen 203 extends substantially through the full length of the proximal part 118, through the arcuate section 122, and joins with the distal needle lumen 132.

Figure 37:
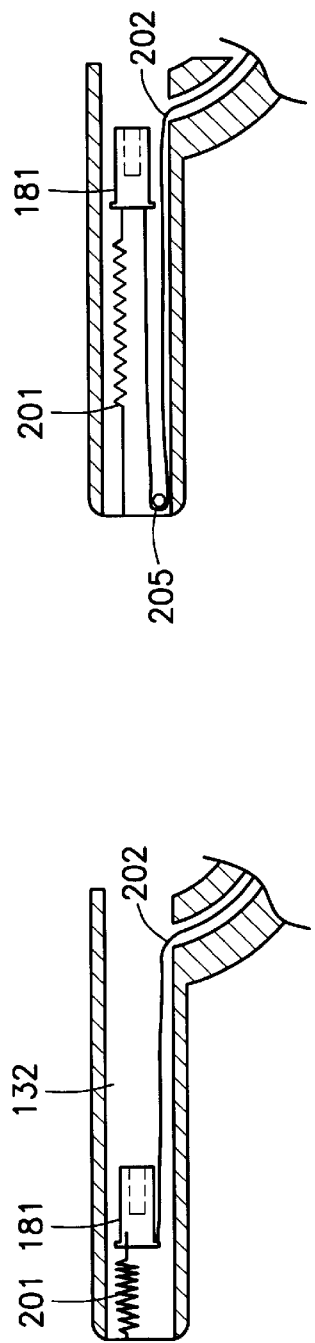
FIG. 37 shows a side cross-sectional view of the distal section of a device according to a sixth embodiment of the invention.
Figure 39:
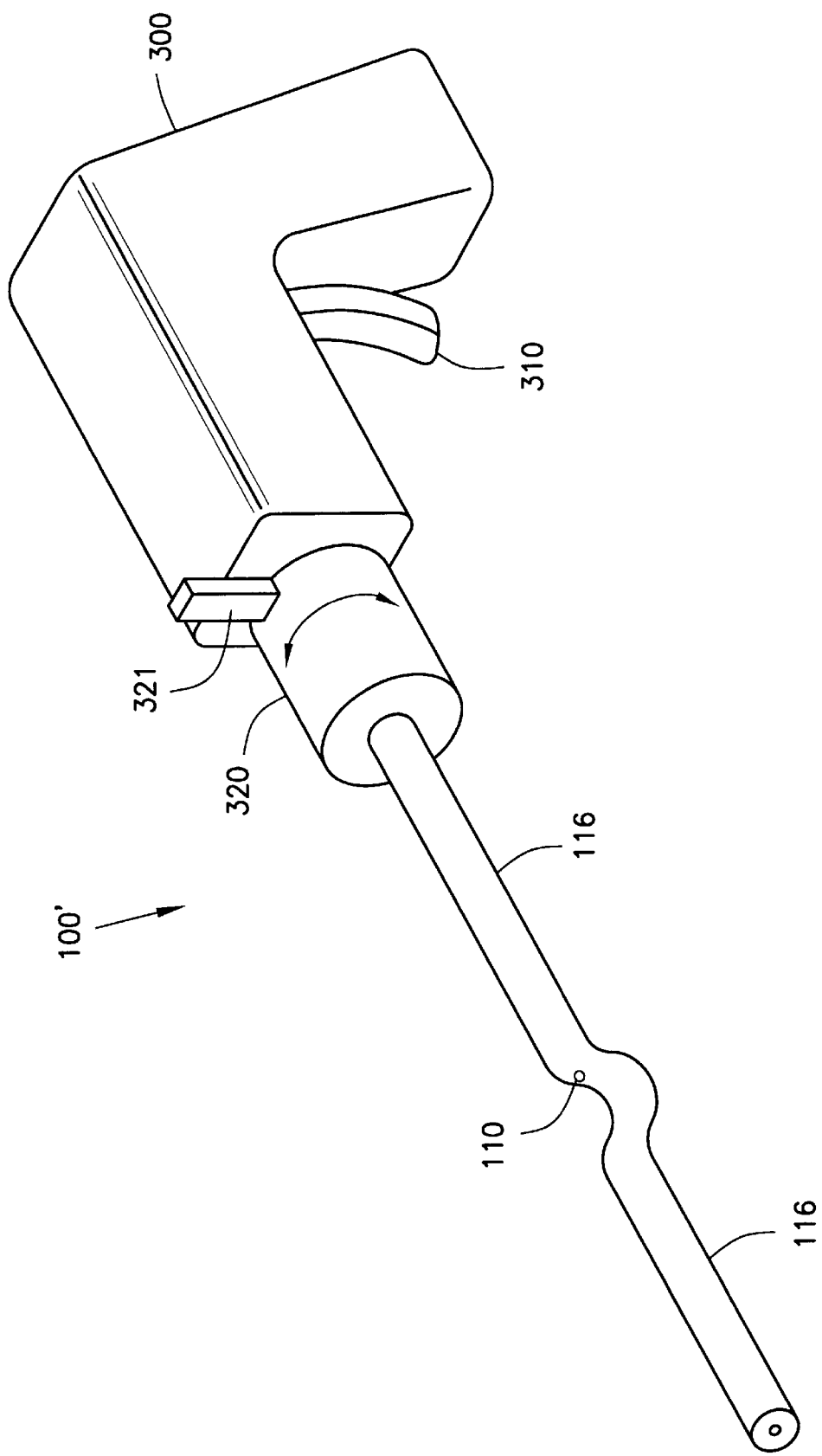
FIG. 39 shows a perspective view of a device according to a seventh embodiment of the present invention.

The distal needle lumen 132 preferably contains a distal needle pusher 181 to push the needle 137 from the distal needle lumen 132 across the gap 94 and back into the proximal needle lumen 126. A rearward end of the distal needle pusher 181, as shown in FIG. 37, is coupled to a spring 201. The distal needle pusher 181 is also coupled to a cable 202, which extends from the distal needle pusher 181 through the cable lumen 203 and out of the proximal end of the device 100 wherein the user has access thereto. In a needle receiving position, the distal needle pusher 181 is positioned in a distal end of the distal part 116.

According to one embodiment, as shown in FIG. 37, spring 201 retains the distal needle pusher 181 in the distal end of the distal needle lumen 132. Thus, a needle 137 may be pushed into the distal needle lumen 132 by the proximal needle pusher 182 without being opposed by the distal needle pusher 181. After the entire length of the needle 137 has been pushed into the distal needle lumen 132, the user repositions the device 100 so that the arcuate section 122 straddles a second portion of the tissue surrounding the hole in the blood vessel 90. The user then pulls the cable 202 to move the distal needle pusher 181 proximally, thereby driving the needle 137 across the gap 94 through the second portion of the blood vessel 90 and into the proximal needle lumen 126. The cable 202 may then be released so that the distal spring 201, which has been extended by the tension on the cable 202, retracts to its non-stressed position pulling the distal needle pusher 181 distally into the distal needle lumen 132.

As shown in FIG. 29, the distal needle lumen 132 may have a stylized cross section adapted for a particularly shaped distal needle pusher 181. For example, the cross section of the distal needle lumen 132 shown in FIG. 29 provides a tab section 186 to allow for the passage of a tab 187 of the distal needle pusher 181. The tab 187, for example, helps keep the distal needle pusher 181 in alignment within the distal needle lumen 132. The cross section of the distal needle lumen 132 may take different shapes at different locations as shown in FIG. 30, such that, for example, the tab section 186 narrows to create a stop 188 through which the distal needle pusher 181 will not pass.

Figure 32:
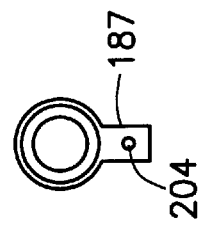
FIG. 32 shows a side view of a distal needle pusher according to the sixth embodiment of the present invention.

As shown in FIG. 32, the distal needle pusher 181 may also contain a cavity 189 adapted to receive the needle 137. The needle 137 may be partially contained within the cavity 189 so that the distal needle pusher 181 can stabilize and guide the needle 137 as the needle 137 is pushed proximally by the distal needle pusher 181 back into the proximal needle lumen 126.

Figure 33:
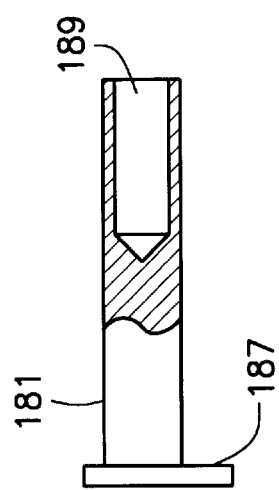
FIG. 33 shows a front view of the distal needle pusher of FIG. 32.

In addition, as shown in FIG. 33, the distal needle pusher 181 may also include a tab 187 that conforms to the shape of the distal needle lumen 132. The shape of the distal needle pusher 181 helps keep the distal needle pusher 181 in proper alignment as it moves within the distal needle lumen 132. The tab 187 may advantageously have a cable orifice 204 that provides a convenient means for attaching the cable 202 to the distal needle pusher 181, or alternatively may provide a passage so that the cable 202 can pass through the distal needle pusher 181 for attachment at a different location on the distal needle pusher 181.

Figure 38:
FIG. 38 shows a side, cross-sectional view of the distal section of a device according to a variation of the sixth embodiment of the invention.

FIG. 38 shows an alternative embodiment to that of FIG. 37. FIG. 38 shows a distal needle pusher 181 coupled to a spring 201 which, in its non-stressed state, maintains the distal needle pusher 181 in the proximal section of the distal needle lumen 132. The cable 202 extends around anchor point 205 at the distal end of the distal needle lumen 132, looping back to attach to the distal needle pusher 181. In this way, tension on the cable 202 draws the distal needle pusher 181 away from the proximal section of the distal needle lumen 132 toward the distal end of the distal needle lumen 132. Pulling the cable 202 to draw the distal needle pusher 181 to the distal end of the distal needle lumen 132 prepares the distal needle lumen 132 to receive the needle 137. Tension must be maintained on cable 202 to maintain the distal needle pusher 181 in the distal end of the distal needle lumen 132.

After a needle 137 has been pushed through the blood vessel wall 90, into the distal needle lumen 132 via the proximal needle pusher 182, the device is rotated to a second position as described in regard to all of the previous embodiments. The tension on the cable 202 may then be released so that the distal spring 201 extends to its neutral position, pushing the distal needle pusher 181 back to the proximal end of the distal needle lumen 132 and driving the needle 137 proximally back across the gap 94 and into the proximal needle lumen 126. The suture 41 and the needle 137 may then be removed from the proximal needle lumen 126 and the ends of the length of suture may then be tied together to seal the opening. Of course, those skilled in the art will understand that the above procedure may be repeated to pass the suture 41 through the blood vessel wall at any number of additional locations before removing the needle 137 and securing the ends of the suture 41 to seal the opening in the blood vessel wall.

Figure 34:
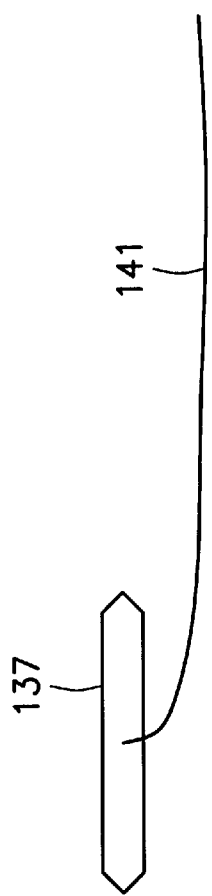
FIG. 34 shows a double pointed needle and suture for use with the device according the sixth embodiment.

A needle 137 adapted for use with this embodiment of the invention may preferably include an anchor, e.g., a hole extending therethrough, for attaching a suture 41 thereto. One embodiment, shown in FIG. 34, provides for a double pointed needle 137 with a suture attached through a middle portion of the needle 137. Thus, the needle 137 may penetrate the blood vessel wall 90 in either direction, pulling the suture 41 through the blood vessel wall 90 from both directions as well. Thus, a single needle 137 may be shuttled back and forth from the proximal needle lumen 126 to the distal needle lumen 132 through the blood vessel wall 90 at any number of positions around the perimeter of the hole in the blood vessel wall 90 without removing the device from the patient's body.

When the needle 137 is substantially contained within the proximal needle lumen 126, the user positions the device so that the opening 110 of the proximal needle lumen 126 and the opening 133 of the distal needle lumen 132 are disposed on opposite sides of a first portion of the blood vessel wall 90 received within the gap 94 created by the arcuate section 122. When the device is in this position, the user pushes the needle 137 and the suture 41 across the gap 94, through the first portion of the blood vessel wall and into the distal needle lumen 132. The user then rotates the device 100 so that a second portion of the blood vessel wall 90 is positioned between the openings 110, 133 and, using the distal needle pusher 181, draws the needle 137 and the suture 41 back from the distal needle lumen 132, through the second portion of the blood vessel wall and into the proximal needle lumen 126. This process is repeated at as many locations as the user desires and the ends of the suture 41 are then coupled together to seal the hole in the blood vessel wall.

FIGS. 39–42 show a device 100' according to another embodiment of the present invention which is substantially similar to the previously discussed embodiment except for the addition of a handle 300 including a mechanism for conveniently manipulating the proximal needle pusher 180, the distal needle pusher 181, and the cable 302 in order to place sutures 41 in a blood vessel wall 90. Cable 302 actuates the distal needle pusher 181 in a manner similar that discussed in reference to FIGS. 28–38, except that the end of cable 302 opposite the distal needle pusher 181 is attached to a trigger mechanism of handle 300 to thereby make the actuation of the cable 302 more convenient.

The main body 116 of device 100' extends distally from a rotatable coupling 320 which is rotatably attached to the handle 300. The coupling 320 may be equipped with a lever 321 to facilitate rotating the coupling 320 relative to the handle 300. Rotating the coupling 320 and hence the main body 116 permits the user to toggle between a proximal-to-distal needle displacement mode and a distal-to-proximal needle displacement mode. That is, when the lever 321 is in a first position, actuation of the trigger 310 moves the proximal needle pusher 182 to drive a needle 137 from the proximal needle lumen 126, across the gap 94, and into the distal needle lumen 132. The user rotates the device so that a second portion of the blood vessel wall is received within the gap 94, as described above, and then moves the lever 321 to a second position to rotates the coupling 320 by approximately 180°. When the lever 321 is in this position, actuation of the trigger 310 actuates the distal needle pusher 181 to move the needle 137 from the distal needle lumen 132 to the proximal needle lumen 126. Of course, those skilled in the art will understand that the trigger 310 may be coupled to the distal needle pusher 181 so that, a distal needle pusher 181, normally maintained at the distal end of the distal needle lumen 132 against the bias of the spring 202, is released to move proximally when the trigger 310 is actuated while the lever is in the second position.

Figure 40:
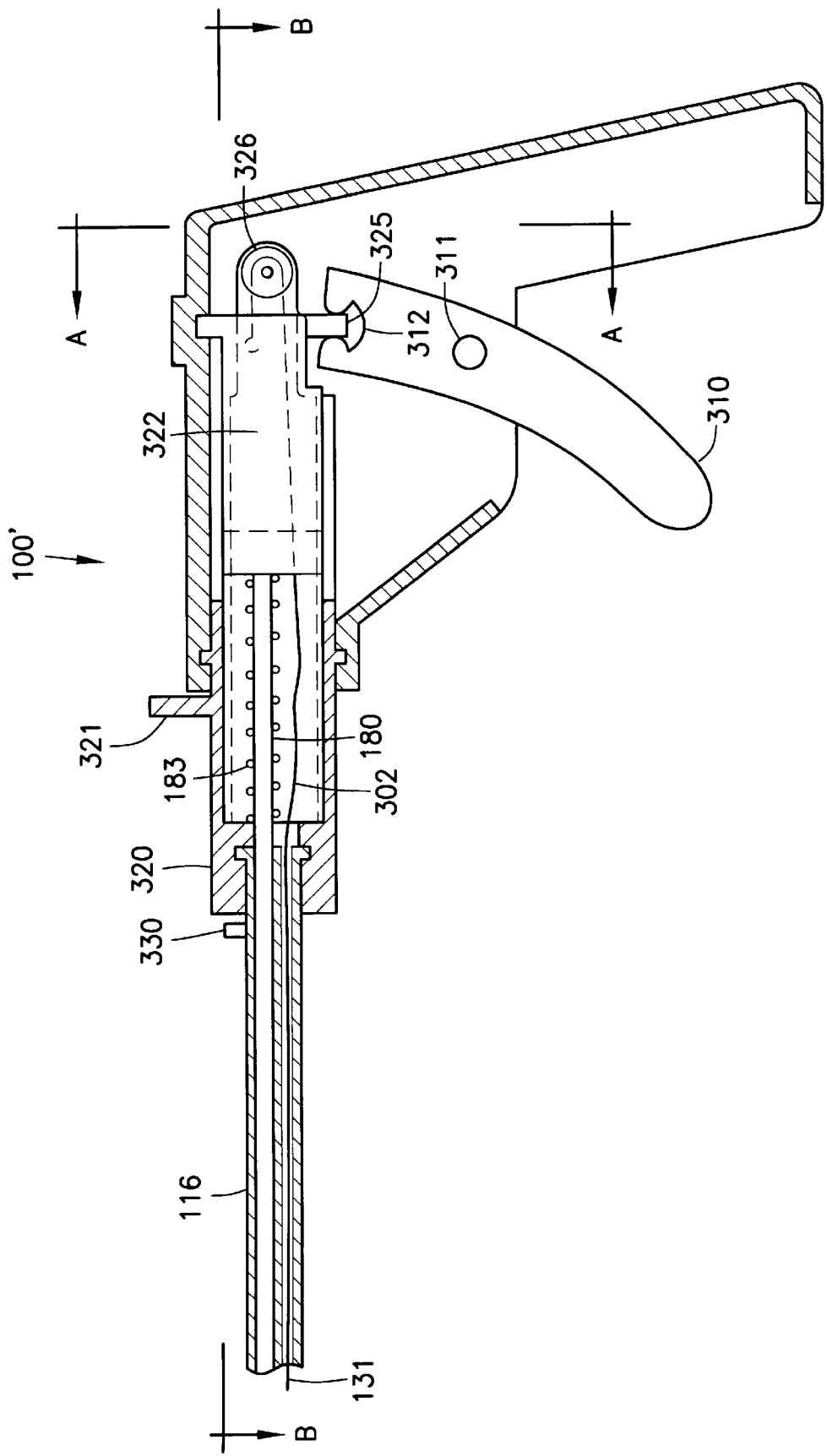
FIG. 40 shows a side, cross-sectional view of the proximal portion of the device of FIG. 39.

As shown in FIGS. 40–42, the handle 300 includes a trigger 310 for actuating the distal needle pusher 181 and the proximal needle pusher 180. The trigger 310 is pivotally mounted to the handle 300 at pivot point 311 with one end of the trigger 310 being accessible to the user while the other end of the trigger 310 may be selectively connected to either a push plate 322 or a pull plate 323. The push plate 322 pushes the proximal needle pusher 180 and the needle 137 across the gap 94, through the blood vessel wall 90 and into the distal needle lumen 132. The pull plate 323 is connected to a cable 302 which pulls the distal needle pusher 181 in order to return the needle 137 from the distal needle lumen 132 to the proximal needle lumen 126. The push plate 322 and the pull plate 323 may both preferably have a construction substantially as shown in FIG. 42.

The user connects the trigger 310 to the pull plate 323 by rotating the pull/push plate assembly 324 via handle 321 and rotatable coupling 320 so that a recess 312 in the trigger 310 receives a tab 325 of the pull plate 323. Thus, when the user pivots the trigger 310 about the pivot point 311, the pull plate 323 is moved distally within the main body 116. When the lever 321 is in the second position, the pull plate 323 is coupled to the cable 302, which loops around pulley 326 before connecting to the distal needle pusher 181. To couple the trigger 310 to the push plate 322, the user rotates the pull/push plate assembly 324 via the handle 321 so that the tab 325' of the push plate 322 is received in the recess 312. Then, when the trigger 310 is actuated, the push plate 322 moves distally to push the proximal needle pusher 180 distally through the proximal needle lumen 126.

Figure 43:
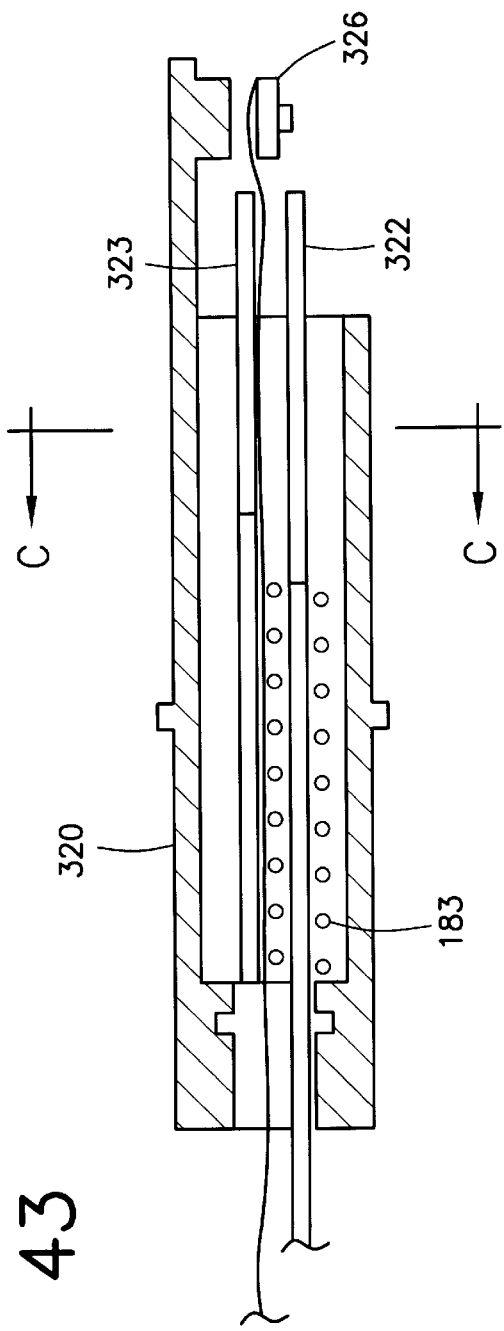
FIG. 43 shows a cross-section of the device of FIG. 40 taken along line B—B.
Figure 44:
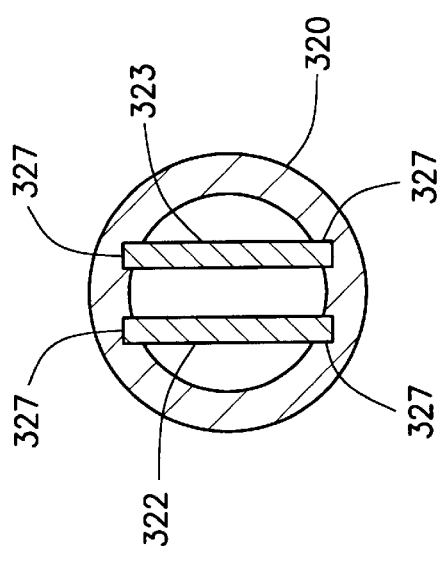
FIG. 44 shows a cross-section of the device of FIG. 43 taken along line C—C.

As shown in FIG. 43, the push plate 322 is held within the rotatable coupling 320 such that it lines up with the proximal needle pusher 180. The pull plate 323, however, has a connection to the cable 302 which extends from the pull plate 323, around the pulley 326 and through the cable lumen 203 to the distal needle pusher 181. The push plate 322 and pull plate 323 are slidably received within the rotatable coupling 320 by, for example, grooves 327, as shown in FIG. 44.

The operation of the distal needle pusher 181 is substantially the same as described with reference to the embodiment of FIGS. 28 and 32 except that it is actuated by the manipulation of the handle and not by a pulling force directly applied by a user to the cable 302. As in the above-described embodiment, the cable 302 may be configured so that the distal needle pusher 181 is generally biased toward the proximal end of the distal needle lumen 132 and is pulled distally away from the gap 94 when the trigger 310 is actuated and vice versa, using mechanisms similar to those described above.

Alternative configurations may be envisioned which remain within the scope of the invention. For example, it may be desirable to configure the rotatable coupling 320 in a manner that rotates the push plate 322 and pull plate 323 relative to the trigger 310, so that the user may alternate between activating the distal needle pusher 181 and the proximal needle pusher 180 as discussed above, while allowing the main body 116 to rotate separately within the rotatable coupling 320. This adds an additional degree of freedom whereby the rotational position of the arcuate section 122 may be oriented at any rotational position relative to the rotatable coupling 320 which in turn may be positioned as required relative to the trigger 310 for activation of the push and pull plates 322, 323, respectively. For this purpose, an optional tab 330, shown in FIG. 40, may be provided on the main body 116 to rotate the main body 116 relative to the rotatable coupling 320.

Those skilled in the art will understand that in sealing blood vessels 90 it is preferable that the cross-sectional area of at least the distal end 24 and the central portion 22 of the device have a cross sectional area substantially uniform along the length of these parts. Since the distal end 24 and central portion 22 of the device are the only parts to enter the blood vessel 90, the uniformity of the cross-sectional area will prevent blood leakage around the perimeter of the device 2, and will also ensure that the appropriate amount of vessel wall is captured by the needles. That is, as the cross-sectional area of the central portion 22 will be selected to completely fill the puncture in the blood vessel, when the central portion 22 is received in the puncture, the needles crossing the gap will pass through a portion of the blood vessel wall separated from the edge of the puncture by a distance substantially equal to the depth of the gap—i.e., the radius of the arc of the central portion. Thus, the distal and central parts of the device 2 may preferably have a cross-sectional area substantially equal to the cross-sectional area of the introducer sheath that has been used during the catheterization procedure.

There are many variations of the above described embodiments which will be apparent to those skilled in the art. It is understood that these modifications are within the teaching of the present invention which is to be limited only by the claims appended hereto. In addition, although the operation of the various embodiments has been described in regard to the sealing of an opening in the wall of a blood vessel, those skilled in the art will understand that this invention may also be used to seal openings in various internal organs and structures.

What is claimed is:

1. A suturing device comprising:
   a proximal part including a needle insertion channel extending therethrough to a needle exit opening formed in a distal end of the proximal part;
   a central part extending distally from the distal end of the proximal part and forming a tissue receiving gap between a distal end of the central part and the distal end of the proximal part, the central part including a needle entry opening formed in the distal end thereof;
   a flexible distal part coupled to the distal end of the central part and having a needle receiving lumen extending from the needle entry opening through at least a portion of the distal part; and
   a needle having a length of suture attached thereto, the needle being slidably insertable through the needle insertion channel to pass through the needle exit opening, cross the tissue receiving gap and enter the needle receiving lumen via the needle entry opening, wherein the needle receiving lumen is sized so that the entire needle may be received therein.

2. The suturing device according to claim 1, further comprising a needle pushing member slidably insertable in the needle insertion channel proximally of the needle so that, upon advancing the needle pushing member distally through the needle insertion channel, a distal end of the needle pushing member abuts a proximal end of the needle to push the needle distally through the needle insertion channel, out of the needle exit opening, across the gap and into the needle receiving lumen via the needle entry opening.

3. The suturing device according to claim 1, wherein the needle includes a sharpened distal tip and a sharpened proximal tip, the device further including a needle pushing mechanism mounted in the distal part to return the needle from the distal part, across the gap into the needle insertion channel.

4. The suturing device according to claim 1, further including a flash back lumen extending from the proximal end of the proximal part to a blood entry opening formed in the central part.

5. The suturing device according to claim 4, wherein the flash back lumen communicates with the needle receiving lumen so that the needle entry opening forms the blood entry opening.

6. The suturing device according to claim 2, further comprising a spring biasing the needle pushing member proximally.

7. The suturing device according to claim 2, further comprising a handle coupled to the proximal end of the proximal part and an actuating member which, when moved to a needle insertion position, advances the needle pushing member distally through the needle insertion channel.

8. The suturing device according to claim 1, wherein the distal part is more flexible than the central part.

9. The suturing device according to claim 8, wherein the distal part is formed of a first material and the central part is formed of a second material different from the first material.

10. The suturing device according to claim 8, wherein the distal part is more flexible than the proximal part.

11. The suturing device according to claim 8, wherein the needle exit opening is fixed with respect to the needle entry opening.

12. A method of suturing a puncture in a blood vessel, comprising the steps of:
    inserting into the puncture a device forming a tissue receiving gap between proximal and distal parts thereof so that a first portion of blood vessel wall adjacent to the tissue is received within the gap;
    moving a needle having a length of suture attached distally through a needle insertion channel formed in the proximal part of the device so that the needle and the length of suture exit the needle insertion channel, pass through the first portion of the blood vessel wall and enter a needle receiving lumen formed in the distal part of the device;
    rotating the device so that a second portion of the blood vessel wall adjacent to the puncture is received within the gap;
    withdrawing the needle proximally from the needle receiving lumen so that the needle and the length of suture exit the needle receiving lumen, pass through the second portion of the blood vessel wall and re-enter the needle insertion channel; and
    coupling ends of the length of suture together to seal the puncture.

13. The method according to claim 12, wherein the step of withdrawing the needle is performed by actuating a needle pushing mechanism mounted in the distal part of the device.

* * * * *